United States Patent
Ezan et al.

(10) Patent No.: US 7,396,691 B2
(45) Date of Patent: Jul. 8, 2008

(54) METHOD FOR THE DETECTION OF FLUORIDE OR HYDROGEN FLUORIDE AND DETECTION KIT

(75) Inventors: Eric Ezan, Malakoff (FR);
Marie-Astrid Sagot, Abbeville la Riviere (FR); Philippe Pradelles, Villebon sur Yvette (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/524,207

(22) PCT Filed: May 14, 2004

(86) PCT No.: PCT/FR2004/050194
§ 371 (c)(1),
(2), (4) Date: Feb. 10, 2005

(87) PCT Pub. No.: WO2004/104579
PCT Pub. Date: Dec. 2, 2004

(65) Prior Publication Data
US 2005/0227368 A1     Oct. 13, 2005

(30) Foreign Application Priority Data
May 20, 2003   (FR)   .................................. 03 50160
May 22, 2003   (FR)   .................................. 03 50167

(51) Int. Cl.
*G01N 33/544*   (2006.01)
*G01N 33/532*   (2006.01)
*G01N 33/53*    (2006.01)
*C07K 1/10*     (2006.01)
*C01B 15/14*    (2006.01)

(52) U.S. Cl. .................. 436/528; 436/544; 436/125; 436/161; 435/7.1; 423/325; 530/402; 530/406

(58) Field of Classification Search ................ 436/527, 436/544, 125, 161, 528; 435/7.1, 961, 975; 423/325; 530/402, 406
See application file for complete search history.

(56) References Cited

U.S. PATENT DOCUMENTS
5,047,300 A    9/1991    Juergens

FOREIGN PATENT DOCUMENTS
| EP | 0 139 552 | 5/1985 |
| JP | 2003 043025 | 2/2003 |
| WO | 03/065408 | 8/2003 |

OTHER PUBLICATIONS

Webster's II New Riverside University Dictionary 1994 Houghton Mifflin Company. pp. 1106 and 120.*

(Continued)

*Primary Examiner*—Long V. Le
*Assistant Examiner*—Shafiqul Haq
(74) *Attorney, Agent, or Firm*—Oblon, Spivak, McClelland, Maier & Neustadt, P.C.

(57) ABSTRACT

The present invention relates to a method for detecting and/or measuring the concentration of fluoride ($F^-$) or hydrogen fluoride (HF) in a sample, comprising the steps consisting of bringing said sample, in aqueous solution, into contact with a silylated organic compound in order to obtain a measurement solution, with said silylated organic compound being desilylated when it is in the presence of hydrofluoric acid or a fluoride, with the silylated organic compound and the desilylated organic compound being able to be detected and/or measured separately from each other; and detecting and/or measuring, in said measurement solution, the appearance of the desilylated against compound or the disappearance of the silylated organic compound, which takes place if fluoride or hydrogen fluoride is present in the sample. The method enables the presence of hydrogen fluoride or of fluorine to be detected very easily and expediently at concentrations of $10^{-2}$ l of HF/$10^6$ l of air (10 ppb) or else of 0.5 to 1 µg/ml of HF in solution. The kit of the present invention comprises the components which are required for implementing this method. The method of the invention makes it possible to detect fluorine at concentrations of the order of 0.001 µg/ml.

13 Claims, 10 Drawing Sheets

OTHER PUBLICATIONS

Wen, M.L. et al. "Developments in the Analysis of Fluoride 1995-1997", Fluoride, vol. 31, No. 2, pp. 74-80 1998.

"Fluoride (F⁻ and HF) in Workplace Atmospheres", Occupational Safety and Health Administration, http://www.osha-slc.gov/dts/sltc/methods/inorganic/id110.html.

Vasiliev, Alexei et al. "High temperature semiconductor sensor for the detection of fluorine", Sensors and Actuators B, vol. 49, pp. 133-138 1998.

"OEM Fluorine Sensor", http://www.bionics-instrument.com/p_fluorine.htm.

Ezan, Eric et al. "Pharmacokinetics in Healthy Volunteers and Patients of NAc-SDKP (Seraspenide), A Negative Regulator of Hematopoiesis", Drug Metabolism and Disposition, vol. 22, No. 6, pp. 843-848.

Shi, Run Zhang et al. "Development of an enzyme-linked immunosorbent assay with monoclonal antibody for quantification of homovanillic in human urine samples", Clinical Chemistry, vol. 44, No. 8, pp. 1674-1679 1998.

Taran, Frederic et al. "Competitive enzyme immunoassay for urinary vanillylmandelic acid", Clinica Chimica Acta, vol. 264, pp. 177-192 1997.

Boschelli, Diane et al. "Synthesis of Amphotericin B. 2. Fragment C-D of the Aglycone", Tetrahedron Letters, vol. 26, No. 43, pp. 5239-5242 1985.

Machard, Sophie et al. "A Sensitive Amphotericin B Immunoassay for Pharmacokinetic and Distribution Studies", Antimicrobial Agents and Chemotherapy, vol. 44, No. 3, pp. 546-550 2000.

Cleary, John D. et al. "Amphotericin B Enzyme-Linked Immunosorbent Assay", Antimicrobial Agents and Chemotherapy, vol. 40, No. 3, pp. 637-641 1996.

Fitzgerald, Robert L. et al. "Serum total testosterone: immunoassay compared with negative chemical ionization gas chromatography-mass spectrometry", Clinical Chemistry, vol. 42, No. 5, pp. 749-755.

Luceri, Francesca et al. "Gas Chromatography-Mass Spectrometry Measurement of 6beta-OH-Cortisol/Cortisol Ratio in Human Urine: A Specific Marker of Enzymatic Induction", Clin. Chem. Lab. Med., vol. 39, No. 12, pp. 1234-1239 2001.

Munro, C.J. et al. "Relationship of Serum Estradiol and Progesterone Concentrations to the Excretion Profiles of Their Major Urinary Metabolites as Measured by Enzyme Immunoassay and Radioimmunoassay", Clin. Chem., vol. 37, No. 6, pp. 838-844 1991.

Metaye, T. et al. "Comparative measurement of progesterone receptors in breast cancer by biochemical and immunoenzymatic assays", Ann. Biol. Clin., vol. 48, pp. 732-736 1990.

Foekens, John A. et al. "Comparison of Enzyme Immunoassay and Dextran-Coated Charcoal Techniques for Progesterone Receptor Determination in Human Breast Cancer Cytosols", J. Steroid Biochem., vol. 29, No. 6, pp. 571-574 1988.

Hosoda, Hiroshi et al. "Sensitivity of Steroid Enzyme Immunoassays. Comparison of Four Label Enzymes in an Assay System Using a Monoclonal Anti-steroid Antibody", Chem. Pharm. Bull., vol. 37, No. 7, pp. 1834-1837 1989.

Hubl, Walter et al. "An Improved Solid-Phase Enzyme and Luminescent Immunoassay System for Steroid Hormones and Digoxin", Clin. Chem., vol. 34, No. 12, pp. 2521-2523 1988.

Hocart, Charles et al. "Mass Spectrometry and Chromatography of t-Butyldimethylsilyl Derivatives of Cytokinin Bases", Analytical Biochemistry, vol. 153, pp. 85-96 1986.

Garcia de Salamone, Ines et al. "Cytokinin production by plant growth promoting rhizobacteria and selected mutants", Can. J. Microbiol., vol. 47, pp. 404-411 2001.

Trione, E.J. et al. "A Quantitative Fluorescence Enzyme Immunoassay for Plant Cytokinins", Analytical Biochemistry, vol. 162, pp. 301-308 1987.

Steffenrud, S. et al. "Gas Chromatography-Mass Spectrometry of Monohydroxyelcosatetraenoic Acids as their Methyl Esters Trimethylsilyl, Allyldimethylsilyl and tert.-Butyldimethylsilyl Ethers", Journal of Chromatography, vol. 416, pp. 219-235 1987.

Smith, BJ et al. "Measurement of Plasma Prostaglandin E2 Using Capillary Gas Chromatography Negative Ion Chemical Ionization Mass Spectrometry", Research Communications in Chemical Pathology and Pharmacology, vol. 40, No. 1, pp. 73-86 1983.

Percival, M. David. "Continuous spectrophotometric assay amenable to 96-well plate format for prostaglandin E synthase activity", Analytical Biochemistry, vol. 313, pp. 307-310 2003.

Hoffman, Stuart W. et al. "A reliable and sensitive enzyme immunoassay method for measuring 8-isoprostaglandin F2alpha: a marker for lipid peroxidation after experimental brain injury", Journal of Neuroscience Methods, vol. 68, pp. 133-136 1996.

Knapp, Daniel R. "Handbook of Analytical Derivatization Reactions", John Wiley and Sons, pp. 8-10, 343-344, 532-535 1979.

Lau, H. Lorrin. "Factors and Artifacts in the Formation of the Trimethylsilyl Ethers of Steroids", J. of G.C., vol. 4, pp. 136-139 1966.

Tallent, W.H. et al. "Bis(trimethylsilyl)acetamide in the silylation of lipolysis products for gas-liquid chromatography", Journal of Lipid Research, vol. 9, pp. 146-148 1968.

Mawhinney, Thomas P. et al. "Gas-Liquid Chromatography and Mass Spectral Analysis of Mono-, Di- and Tricarboxylates as Their tert.-Butyldlmethylsilyl Derivatives", Journal of Chromatography, vol. 361, pp. 117-130 1986.

Mawhinney, Thomas P. "Simultaneous Determination of N-Acetylglucosamine, N-Acetylgalactosamine, N-Acetylglucosaminitol and N-Ace-Tylgalactosaminitol by Gas-Liquid Chromatography", Journal of Chromatography, vol. 351, pp. 91-102 1986.

Bazan, A.C. et al. "Improved derivative of 6-keto-prostaglandin F1alpha for gas chromato-graphic-mass spectrometric analysis", Journal of Chromatography, vol. 236, pp. 201-207 1982.

Dehennin, Louis. "Estradiol-17beta Determined in Plasma by Gas Chromatography-Mass Spectrometry with Selected Ion Monitoring of Mixed Silyl Ether-Perfluoroacyl Ester Derivatives and Use of Various Stable-Isotope-Labeled Internal Standards", Clin. Chem., vol. 35, No. 4, pp. 532-536 1989.

Andersson, S.H.G. et al. "Analysis of Profiles of Unconjugated Steroids in Rat Testicular Tissue by Gas Chromatography-Mass Spectrometry", J. Steroid Biochem., vol. 23, No. 4 , pp. 469-475 1985.

Ishikawa, Eiji et al. "Development and Applications of Sensitive Enzyme Immunoassay for Antibodies: A Review", Journal of Clinical Laboratory Analysis, vol. 3, pp. 252-265 1989.

Ishikawa, Eiji. "Development and Clinical Application of Sensitive Enzyme Immunoassay for Macromolecular Antigens-A Review", Clinical Biochemistry, vol. 20, pp. 375-385 1987.

Oellerich, M. "Enzyme-Immunoassay: A Review", J. Clin. Chem. Clin. Biochem., vol. 22, No. 12, pp. 895-904 1984.

O'Sullivan, M.J. et al. "Enzyme immunoassay: a review", Annals of Clinical Biochemistry, vol. 16, pp. 221-240 1979.

Ezan, E. et al. "Strategies for Developing Specific and Sensitive Hapten Radioimmunoassays", Handbook of Pharmacology: Radioimmunoassay in basic and clinical pharmacology, Chapter 6, pp. 143-179 1987.

Buscarlet, Laure et al. "Cross-Linking of 17beta-Estradiol to Monoclonal Antibodies By Direct UV Irradiation: Application to an Enzyme Immunometric Assay", Anal. Chem., vol. 71, No. 5, pp. 1002-1008 1999.

Nakagomi, Madoka et al. "Enzyme immunoassay for the measurement of alpha-estradiol 17-N-acetylglucosaminide in rabbit urine", Steroids, vol. 64, pp. 301-307 1999.

El Jabri, Jamila. "Enzyme Immunoassay for Plasma Estradiol Using a Monoclonal Antibody", J. Steroid Biochem. Molec. Biol., vol. 38, No. 3, pp. 339-343 1991.

Dhar, Tarun et al. "Homogeneous Enzyme Immunoassay of Estradiol-3-O-Carboxymethyl Ether as Hapten", Steroids, vol. 51, No. 5-6, pp. 519-526 1988.

Ellman, George L. et al. "A New and Rapid Colorimetric Determination of Acetylcholinesterase Activity", Biochemical Pharmacology, vol. 7, pp. 88-95 .

Descalzo, Ana B et al: "A new method for fluoride determination by using fluorophores and dyes anchored onto MCM-14" Chem. Commu., vol. 6 pp. 562-563, Mar. 11, 2002.

Choi, Man Ho et al. "Determination of estrone and 17beta-estradiol in human hair by gas chromatography-mass spectrometry", Analyst, vol. 125, pp. 711-714, 2000.

* cited by examiner

METHOD FOR THE DETECTION OF FLUORIDE OR HYDROGEN FLUORIDE AND DETECTION KIT

TECHNICAL FIELD

The present invention relates to a method for detecting and/or measuring the concentration of fluoride ($F^-$) or hydrogen fluoride (HF) which is present in a sample and to a detection kit for implementing this method. This invention makes it possible to measure an environmental pollutant efficiently and sensitively. The invention is based on a method which is entirely original and is easy to implement.

Hydrogen fluoride is a strong inorganic acid which is colorless and very soluble in water, where it forms hydrofluoric acid. HF is a gas which is widely used in industry, in particular for producing polymers, cooling liquids and fire-extinguishing products, for refining aluminum, for preparing nuclear fuels and for manufacturing components for electronics. In addition, it is a product which is emitted during the combustion of coal, household or industrial wastes and plastics.

HF is toxic above concentrations of the order of $3\times10^{-2}$ l of $HF/10^6$ l of air (30 ppm). HF is a powerful irritant which can cause burns, resulting from exposure of the skin/mucous membranes, as well as inflammation of the upper and lower airways. In addition, its absorption can give rise to metabolic disturbances.

Furthermore, this product is very corrosive in regard to a large number of materials such as iron, bronze and glass.

The protection of people, of the environment and of industrial equipment consequently makes it necessary to set up means for monitoring its concentration, particularly in industrial effluents and in laboratories, as well as in the atmosphere surrounding these installations, in order to be able to take appropriate measures if dangerous concentrations of HF are detected.

Norms for acceptable atmospheric concentrations of HF have been established in a large number of countries. These norms are generally between $5\times10^{-5}$ and $5\times10^{-4}$ l of $HF/10^6$ l of air (between 0.05 and 0.5 ppm).

In the remainder of the description, the references between square brackets [ ] refer to the reference list which is appended hereto.

PRIOR ART

To date, a large number of methods have been developed, and described, for measuring HF or fluoride ions. In general, these techniques are based on chemical, electrochemical, spectrometric or optical detection. A large number of devices which can be used for detecting and measuring the quantity of HF are available commercially.

Document [1] in the appended reference list describes a number of electrochemical, spectrophotometric and chromatographic methods which can be used for detecting and measuring the quantity of HF in a sample.

A reference method, termed ID-110, which is based on using specific electrodes is described on the OSHA website with the reference number [2]. While the sensitivity of this method is $1.2\times10^{-2}$ l of $HF/10^6$ l of air (12 ppb), the method is a laboratory test which is difficult to apply in the field. As far as field methods are concerned, they are much less sensitive and of the order of 0.2 l of $HF/10^6$ l of air (200 ppb).

Another method uses a detector which is based on a silicon carbide substrate ("Metal Insulator Semiconductor": MIS). This method is described, for example, in the document with the reference number [3]. Various manufacturers propose a variety of electronic detection instruments for measuring HF. Examples of these are the OEM Fluorine Sensor (trade mark) instrument from the Bionics Instrument company and which is described on the website with the reference. [4], or the LaserGas (trade mark) instrument from the NORSK ELEKTRO OPTIKK A/S company.

The detection limits which are given for these instruments are expressed in parts per million or parts per billion (ppm or ppb) in the case of a gaseous medium or as nanograms or micrograms per milliliter (ng/ml or µg/ml) in the case of an aqueous medium. In general, the limits are of the order of $10^{-4}$ l of $HF/10^6$ l of air (0.1 ppm) or, when in solution, of from 1 to 1000 ng of HF/ml in the case of the best systems.

Unfortunately, these methods and instruments require space, are difficult to move about, are sometimes difficult to implement and are frequently expensive.

A "ideal means for detecting" HF should combine the following features:
sensitivity: measurement of at least $10^{-4}$ l of $HF/10^6$ l of air (0.1 ppm),
cost: this should not be too high in order to make it possible, if necessary, to readily increase the number of detectors,
availability: a number of published techniques are not available on the market, particularly because of the difficulty in implementing them,
mobility: it should be possible to easily move the means, in order to be able to use it at different sites,
rapidity of implementation, and of the use of the results.

It appears that none of the methods or devices of the prior art combines all these properties.

There is therefore a real need for novel techniques which combine as many as possible of the above mentioned features of the "ideal detection means".

ACCOUNT OF THE INVENTION

The object which is achieved by the present invention is specifically that of supplying a method and a kit for detecting HF, which method and kit possess all the abovementioned features and furthermore do not suffer from the abovementioned drawbacks of the methods and devices of the prior art.

This object is achieved by means of a method for detecting and/or measuring the concentration of fluoride ($F^-$) or hydrogen fluoride (HF) in a sample, which method comprises the following steps:
bringing said sample, in aqueous solution, into contact with a silylated organic compound in order to obtain a measurement solution, with said silylated organic compound being desilylated when it is in the presence of hydrofluoric acid or of fluoride, with the silylated organic compound and the desilylated organic compound being able to be detected and/or measured separately from each other; and
detecting and/or measuring, in said measurement solution, the appearance of the desilylated organic compound, or the disappearance of the silylated organic compound, which takes place if fluoride or hydrogen fluoride is present in the sample.

In the description which follows, fluoride ($F^-$), hydrogen fluoride (HF) and hydrofluoric acid are implicitly designated by the terms "fluorine" or "fluorine and its derivatives". Fluoride(s) is understood as meaning salts of fluorine.

Fluorine is a very nucleophilic atom and, for this reason, it can intervene in nucleophilic substitution reactions. More particularly, it can specifically attack bonds of the silicon-oxygen (Si—O) type in the manner shown in the following chemical equation.

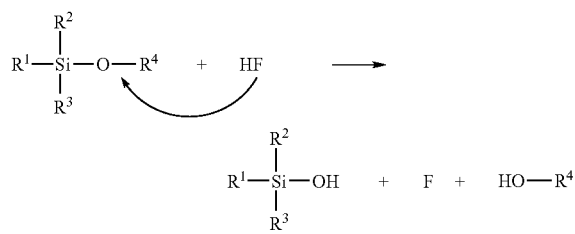

silylated compound $R^4$ hydrogen fluoride silyl group compound $R^4$ (desilylated)

General Principle of the Reaction of HF on the Si—O Bond (Desilylation)

In this chemical equation, $R^1$, $R^2$ and $R^3$ are substituents of Si and form, with the latter, a silylation group of the organic compound $R^4$ within the meaning of the present invention.

$R^1$, $R^2$ and $R^3$ can be selected independently from $C_1$ to $C_6$ alkyls. For example, $R^1$, $R^2$ and $R^3$ can be selected independently from the group consisting of methyl, ethyl, propyl and butyl.

In this chemical equation, —$R^4$ therefore represents the organic compound which is silylated (on the left) or desilylated (on the right) during the implementation of the method of the invention. In order to be able to be silylated, this compound contains at least one hydroxyl function which is accessible for silylation. This compound is advantageously an organic compound in order to facilitate its detection when the method of the invention is implemented. In general, it has a molecular weight of from 250 to 200 000 g.mol$^{-1}$, for example from 250 to 1500 g.mol$^{-1}$, in particular for issues of solubility, and therefore sensitivity, and reproducibility of the fluorine detection and/or measurement results. The compound can be a hydroxylated compound which is selected, for example, from estradiol, peptides, for example peptides containing from 3 to 50 amino acid residues, homovanillic acid, amphotericin, steroids, cytokines and arachidonic acid, or derivatives of these compounds.

A peptide which can be used in the present invention is described, for example, in reference [5]; homovanillic acid which can be used, and derivatives thereof, are described, for example, in references [6] and [7]; amphotericin which can be used is described, for example, in references [8] to [10]; steroids and steroid derivatives which can be used in the present invention are described, for example, in references [11] to [17]; cytokines and cytokine derivatives which can be used in the present invention are described, for example, in references [18] to [20]; and arachidonic acid and its derivatives which can be used are described, for example, in references [21] to [24].

The essential thing is that the silylated organic compound and the desilylated organic compound can be detected and/or measured separately from each other in order to make it possible to detect and/or measure the disappearance of one, and/or the appearance of the other, of these compounds in the measurement solution. Thus, the method of the invention is based on detecting the silylated organic compound or the desilylated organic compound, or these two compounds, but then separately from each other.

According to the invention, any suitable reagent can be used for attaching a silyl group (silylation) to the selected organic compound, provided that the desilylated organic compound, or native form of the organic compound, can be recovered intact by the simple action of fluorine, or its derivatives, on the silylated organic compound. The silyl groups or functions which can be used are described above in the chemical equation.

Mention may be made, by way of example, of the following reagents which can be used for silylating hydroxylated organic compounds for the purpose of implementing the present invention: N,O-bis(trimethylsilyl)trifluoroacetamide (or BTSFA), N-methyl-N-(tert-butyldimethylsilyl)trifluoroacetamide (or MTBSTFA), trimethylsilyl (or TMS), tert-butyldimethylsilyl (or t-BDMS), N,O-bis(trimethylsilyl)acetamide (or BSA), hexamethyldisilazane (or HMDS), N-methyltrimethylsilyl-trifluoroacetamide (or MSTFA), trimethylchlorosilane (or TMCS), trimethylsilylimidazole (or TMSI), etc.

Other reagents and operational modes for silylating which can be used for implementing the present invention can also be found, for example, in references [25] to [30] in the appended reference list.

In general, these reagents are simple to use and readily available and make it possible to transfer a silyl function (containing a silicon atom) onto a hydroxyl function belonging to the selected organic compound.

Mention may be made, in particular, of the following two reagents for the purpose of illustrating the fact that the inventors have additionally, in the present invention, demonstrated a variation in the sensitivity and selectivity of the detection and/or measurement of fluorine in accordance with the invention in dependence on the silyl group which is used:

BTSFA, which attaches a trimethylsilyl (—$Si(CH_3)_3$) function to the —OH groups of the selected organic compound;

MTBSTFA, which attaches a dimethyl tert-butylsilyl (Si$(CH_3)_2C(CH_3)_3$ function to the —OH groups of the selected organic compound.

BTSFA exhibits the advantage of transferring, to the hydroxylated compounds, a silyl which is not particularly hydrophobic, thereby enabling the silylated organic compound to have relatively good solubility. However, the silylated compounds which are obtained do not always exhibit specificity toward HF in regard to their conversion into desilylated compounds when the method of the invention is implemented. They can also be converted into desilylated compounds by other acids which are present in the sample. This reagent can therefore preferably be used for detecting fluorine when specificity in regard to the fluorine is not required or else for detecting fluorine in samples in which the concentration of the other acids is sufficiently low as not to interfere with the detection or the measurement of the fluorine.

MTBSTFA transfers a more hydrophobic silyl group to the hydroxylated compounds and the solubility of the resulting silylated compounds in aqueous medium is less good than in the case of the silylated compounds which are obtained with BTSFA. On the other hand, and quite unexpectedly, the desilylation of the compounds which have been silylated by MTBSTFA is more specific for HF than for the other acids tested, as is demonstrated in the examples. This reagent can therefore advantageously be employed for detecting hydrogen fluoride in a sample when specificity in regard to fluorine is required, for example when the sample contains other acids at concentrations significant.

Thus, the inventors have discovered, in particular by using these reagents, that the specificity of the attack on the Si—O bond by the fluorine also depends on the radicals which are attached to the silicon and oxygen atoms. Thus, when the silylation group is selected appropriately, the other inorganic or organic acids and salts in the sample do not interfere with the measurements which are taken when the method of the invention is implemented. For example, HF has almost the same desilylation activity as HCl when the method of the invention is implemented using —Si—(CH$_3$)$_3$ and an activity which is about 1000 times greater (in the case of HF as compared to HCl) when the method of the invention is implemented using —O—Si—(CH$_3$)$_2$—C(CH$_3$)$_3$.

As the above chemical equation shows, the conversion of the silylated organic compound into a desilylated organic compound by the fluorine or its derivatives is proportional to the quantity of HF which is present in the sample. It is therefore possible, by means of the method of the invention, to detect and measure, at one and the same time, the fluorine and its derivatives which are present in a sample. The essential feature of the invention, and its inventive nature, consist precisely in detecting the fluoride and/or the hydrogen fluoride by using a detection means which measures the difference between the silylated organic compound and the unsilylated (desilylated) organic compound, and therefore detecting/quantifying the desilylation which is catalyzed by the presence of the fluorine.

The step of bringing into contact can be effected by mixing the sample and the silylated organic compound in an aqueous solution. The mixing can be effected by simply adding the sample and the fluorine in solution or by means of active mixing, for example using a mechanical or magnetic stirrer, by means of ultrasonication, etc., of the sample and the fluorine in solution, with the objective naturally being that of promoting the interaction between the fluorine, if it is present, and the silylated organic compound so as to ensure that they react together.

The sample can be a liquid, solid or gaseous sample. When the sample is not liquid, the step of bringing the sample and the silylated organic compound of the method of the invention into contact in aqueous solution naturally comprises dissolving the sample in an aqueous solution, for example by means of bubbling when the sample is gaseous or by means of mixing or solubilizing while stirring when the sample is solid, with the aim of this dissolution being that of once again finding the fluorine of the gaseous or solid sample in the contacting aqueous solution. The methods which are used for this dissolution are well known to the skilled person.

The inventors have demonstrated that the addition of a water-miscible organic solvent to said contacting aqueous solution can substantially increase the sensitivity of the detection and/or measurement of the fluorine by the method of the invention. By way of example, the organic solvent can be selected from dimethylformamide (DMF), dimethyl sulfoxide (DMSO), ethanol or methanol or equivalent organic solvents which are known to the skilled person. Thus, the inventors have measured an increase in the sensitivity of the detection of the fluorine by a factor of 100, and even of 500, when such solvents are used. For example, when using DMSO, the sensitivity of detection extends to 0.001 µg/ml.

The organic solvent could have several different effects: facilitating the solubility of the silylated organic compound, facilitating the desilylation or decreasing interference in the detection (noticed, in particular, in the immunotests). Whatever it may be, one of these effects alone is not sufficient to explain the quite surprisingly significant increase in the sensitivity of detection in the presence of the organic solvent. This organic solvent can be present in a quantity in the range from 1 to 99% by volume of the contacting aqueous solution, advantageously from 50 to 95% by volume of the contacting aqueous solution, with the remainder being water.

The origin of this solvent can advantageously be the recovery solvent of the silylated organic compound after it has been prepared, that is to say after the organic compound has been silylated. The step of bringing into contact can then be effected by mixing the aqueous solution of the fluorine and the organic solution of the silylated organic compound. Otherwise, the organic solvent can be added independently to the contacting solution.

The detection of the silylated organic compound which disappears or of the desilylated organic compound which appears can be effected using any means known to the skilled person which makes it possible to demonstrate the presence of one or other of these compounds separately. The means can, for example, be a detection and/or a measurement which is effected by gas chromatography or a detection and/or a measurement which is effected by means of an immunological test.

For the purpose of carrying out the measurement, a standard series can, in a general manner, be first of all determined by applying the method of the invention using known quantities of hydrofluoric acid or fluorine, or using known quantities of the silylated or unsilylated organic compound. This standard series will then make it possible, by means of simple extrapolation, to determine the quantity of fluorine, of hydrogen fluoride or of hydrofluoric acid which is present in the sample.

In a first embodiment of the present invention, the detection and/or the measurement can be effected by means of gas chromatography. This is because this technique makes it possible to separately detect and/or measure the silylated form or the desilylated form of the organic compound according to the invention and therefore the fluorine if it is present. The chromatographic techniques which can be used are those which are known to the skilled person. The techniques described in references [31] to [33] in the appended reference list may be mentioned by way of example.

The organic compounds which can be used in this first embodiment can be the abovementioned hydroxylated organic compounds. The silylation reagents and techniques can also be those which are mentioned above.

In a second embodiment of the present invention, the detection and/or measurement of the appearance of the unsilylated organic compound or of the disappearance of the silylated organic compound is advantageously effected using an immunological test, that is to say using antibodies which are directed either against the unsilylated organic compound or against the silylated organic compound. No approach of this type is disclosed in the prior art. In addition, this embodiment makes it possible to detect the fluorine much more sensitively than do the techniques of the prior art.

In a general manner, antibodies are proteins which are able, with very great specificity, to recognize, and bind to, structures termed antigens in order to form a detectable antibody/antigen complex. However, since HF is a molecule of very small size, it is impossible to produce antibodies against it. Since they were unable to produce antibodies which are directed directly against HF, the inventors adopted an original strategy based on the abovementioned chemical properties of the fluorine and on using particular silylated organic compounds which exhibit the special feature of giving rise to the generation of antibodies when they are injected into an animal.

The organic compounds which can be used in this second embodiment are organic compounds which possess one or more hydroxyl group(s) which enable a silyl group within the meaning of the present invention to be attached and which induce, in an animal into which they have been injected, the specific production of antibodies which are directed against the silylated organic compound or against the unsilylated organic compound. The organic compounds generally have a molecular weight of from 250 to 200 000 g.mol$^{-1}$, for example from 250 to 1500 g.mol$^{-1}$. The organic compound can, for example, be an organic compound which is selected from the above-mentioned hydroxylated organic compounds, for example selected from estradiol; peptides, for example peptides comprising from 3 to 50 amino acid residues, for example the tetrapeptide acetylated Ser-Asp-Lys-Pro (AcS-DKP), which is mentioned in reference [5]; homovanillic acid; amphotericin; steroids; cytokines; arachidonic acid; or derivatives of these compounds. The organic compounds can, for example, be compounds such as those mentioned in references [5] to [24].

As an illustrative example, it is possible to use estradiol or its derivatives. According to the invention, "estradiol" is understood as meaning, for example, estratiene-1,3,5 diol-3, 17μ or 17μ-diol, or their derivatives, or other, equivalent, compounds, provided they are able to generate the formation of antibodies when they are injected into an animal, for example a mouse, and provided they are able to be silylated within the meaning of the present invention.

Examples of silylated estradiols which have been obtained by the inventors and which can be used in the present invention are depicted below. Estradiol possesses —OH functions to which it is possible to attach a silyl group by means of Si—O bonds, as depicted below (to be compared, for example, to native estradiol (Es), which is depicted in the appended FIG. 1).

The reagents which can be used for silylating the organic compound which is selected for implementing this second embodiment of the present invention can be those mentioned above, for example BTSFA or MTBSTFA.

The antibodies which can be used in this embodiment of the invention exhibit the special feature of recognizing the silylated organic compound and the unsilylated organic compound differently. These antibodies can be monoclonal. They can be prepared by means of the techniques which are customary for preparing antibodies of this type, for example by injecting the silylated organic compound, or else the unsilylated organic compound, into a mouse in order to obtain a mouse antibody which is specific for only one of these compounds. Tests can be carried out on different batches of prepared antibodies in order to select antibodies which are specific for only one of the two compounds (silylated or unsilylated) for the purpose of implementing the method of the invention. The skilled person is familiar with these techniques for preparing antibodies.

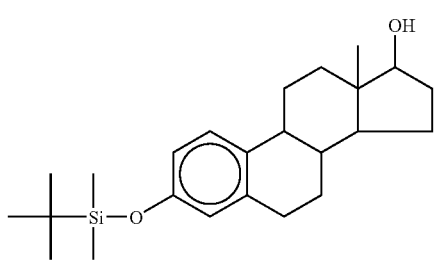

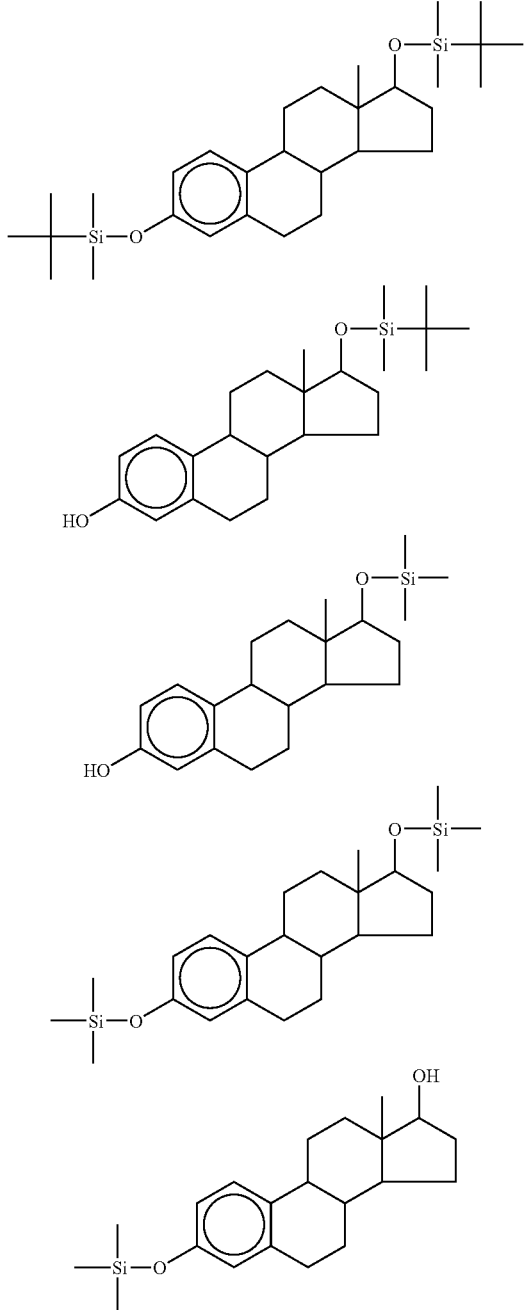

Examples of Silylated Estradiols which can be Used in the Present Invention

By way of example, the documents with the reference numbers [34] to [38] outline appropriate methods for preparing antibodies which can be used for implementing the present invention.

Also by way of example, references [5] to [24] and [39] to [42] additionally describe antibodies which can be used for implementing the present invention when the organic compound is a silylatable compound which is selected from the above list.

In the example which is illustrated by the appended FIG. 1, the antibody which is directed against estradiol and which is used in the immunoassay is selected such that it no longer recognizes estradiol, or recognizes it much less well (i.e. in a manner which is sufficient for this difference in recognition to be detected) when the estradiol is modified with a silyl group (also termed "modified estradiol" below). The effect of the fluorine on the modified estradiol is to attack the Si—O bond (desilylation reaction), thereby enabling the native estradiol to reappear, it then being possible for native estradiol to be recognized by its specific antibody, which is termed "first antibody" below.

Any means for detecting an antigen/antibody recognition which are known to the skilled person can be used in the present invention for detecting either recognition of the desilylated organic compound ("native organic compound") by its antibody or recognition of the silylated organic compound by its antibody. This is the reason why the terms "means for detecting an interaction between a first antibody and the unsilylated organic compound" or "means for detecting an interaction between a first antibody and the silylated organic compound" are used herein. The operational conditions for such detections using antibodies are known to the skilled person. Protocols, reagents, buffers and operational conditions which can be used are described, for example, in the documents with the reference numbers [5] to [24] and [39] to [42].

The detection in accordance with this embodiment can be effected by carrying out an immunoassay of the "competitive" type or of the "noncompetitive" type, for example such as those which are customarily employed in immunological methods of detection and/or immunological methods of measurement.

According to a first variant of this second embodiment of the present invention, the detection means can, for example, be a labeled molecule which is termed a "tracer" and which enters into competition with the silylated or unsilylated organic compound, for example silylated or unsilylated estradiol, in regard to said first antibody. This labeled molecule can use an enzyme, for example acetylcholine esterase, a fluorescent label, a luminescent label or a radioisotope for the detection.

The immunoassay (or immunological measurement) of the silylated or unsilylated organic compound is then said to be "competitive": it makes use of an antibody which is directed against the silylated or unsilylated organic compound, for example silylated or unsilylated estradiol, which is present in a standard series or in a sample, and a tracer which is chemically similar to the organic compound according to the invention, for example estradiol, and which carries a signal (label), for example an enzymic, fluorescent, luminescent or radioactive signal. In the abovementioned example of estradiol, the tracer can be obtained, for example, by coupling the estradiol to an enzyme, for example acetylchloline esterase.

A "competitive" detection which can be used for implementing the method of the invention is depicted diagrammatically in FIGS. 2 and 3. The organic compound which is used in these figures is estradiol. The labeled molecule or tracer is given the reference "T", while unsilylated (unmodified) estradiol is given the reference "Es" and silylated (modified) estradiol is given the reference "Es-M". The first antibody is, for example, a mouse antibody (sAb). FIG. 2 shows that, while modified estradiol (Es-M) cannot be recognized by the antibody (sAb) (this inability is represented by the cross), it is converted, when HF is present, into native estradiol (Es) which can then be recognized by the first antibody (sAb). It then enters into competition with the tracer (T) (labeled estradiol). The presence of HF can therefore be detected. In this method, the quantity of tracer which is bound to the antibody is inversely proportional to the quantity of estradiol which is present in the sample.

In this method of detection by competition, the means for detecting the interaction between the first antibody (sAb) and the unsilylated organic compound (or the means for detecting an interaction between the first antibody and the silylated organic compound) can comprise a second antibody (gAb). For example, this second antibody can be a goat antibody (gAb) or a rabbit antibody which is directed against the above-mentioned mouse antibody (sAb) (first antibody). A diagrammatic depiction of this detection using a second antibody has been added to the appended FIG. 2. This second antibody (gAb) can be bound to the bottom of a receptacle (R), for example a microtitration plate.

In this example, therefore, the assay consists in effecting a competition, between the tracer and the estradiol to be measured, in regard to a limited number of antibody molecules. At the end of the reaction, and after the tracer which is not bound to the antibodies has been removed, the signal carried by the antibody-bound tracer can be measured.

When the tracer comprises an enzyme, for example acetylcholine esterase (shown diagrammatically by the white square in FIG. 2), the detection means can additionally comprise an enzymic indicator. In the abovementioned example of using acetylcholine esterase, the enzymic indicator can consist of a mixture of acetylthiocholine and dithionitrofluorobenzene. This indicator is transformed into a yellow product which is visible to the naked eye or which can be quantified using a spectrophotomer at 414 nm. This indicator is in fact used for applying the Ellman colorimetric detection and measurement method for implementing the present invention. This method is described, for example, in the document with the reference number [43].

According to a second variant of this second embodiment of the present invention, the detection and/or measurement of the fluorine in accordance with the method of the invention is effected using an immunoassay of the "non-competitive" type. As compared to the competitive assay, the difficulty in the non-competitive approach is linked to the selected organic compound, which should possess two chemical properties: the possibility of being coupled to a solid phase and the possibility of being silylated. In addition, having been coupled to the solid phase, the organic compound should be able to be desilylated under conditions which are as advantageous as in liquid phase. This variant can be applied to the abovementioned hydroxylated organic compounds. For example, it can be applied to estradiol derivatives such as those mentioned above, for example estradiol 3-carboxymethyl ether, or to peptides, for example the abovementioned AcSDKP.

In this variant, the silylated compound is coupled to a solid phase, for example a support, for example a microtitration plate such as those which are currently used in laboratories. The sample can be brought into contact with the silylated compound which is thus immobilized on the plate and the detection and/or measurement can be effected in situ.

The silylated compound can be immobilized on, or coupled to, the support by any appropriate technique known to the skilled person for attaching one of the silylated organic compounds as defined above to a support while at the same time preserving the reactivity of the silylated compound with fluoride ions. Everything depends on the chemical nature of the support and of the silylated organic compound which is selected for implementing the present invention. This attachment can be effected, for example, by means of a covalent bond. The support can be a functionalized support, that is a support to which chemical groups facilitating the attachment of the silylated organic compound have been grafted. The support can, for example, be a plate which comprises amino groups, for example a Nunc-NH$_2$ plate, or a plate which is activated with polylysine, for example when the selected silylated organic compound is an estradiol derivative such as those mentioned above, for example estradiol 3-carboxymethyl ether, or a peptide, for example AcSDKP.

Following reaction with the fluoride ions, if they are present in the sample, the silylated compound which is attached to the support is transformed into an unsilylated compound. The detection and/or measurement can then be effected by means of an immunoassay technique, for example in the presence of a first antibody which specifically recognizes the unsilylated compound.

The recognition of the unsilylated compound by the first antibody can be demonstrated by any means known to the skilled person, for example by labeling the first antibody, but also by means of using a second antibody which recognizes the first antibody and which carries a label (the second antibody is then a tracer). The label can, for example, be one of those which are customarily used by the skilled person, for example an enzymic signal. For example, the second antibody can be a goat or rabbit antibody (gAb) which is directed against the first antibody, which can be a mouse antibody (sAb).

One method of "non-competitive" detection is depicted diagrammatically in FIG. 18. The organic compound which is used in this figure is estradiol carboxymethyl ether (Es-tCME). The first of the antibodies employed is an anti-estradiol antibody (for example mouse antibody) which is given the reference "sAb" (tracer). The unsilylated (unmodified) estradiol is given the reference "Es" and the silylated (modified) estradiol is given the reference "Es-M". A second goat or rabbit antibody (gAb), which is directed against the mouse antibody (sAb), is added, for example to the surface of a microtitration plate (R). The gAb antibody is attached to a label, for example an enzyme, in order to form the tracer "T". This figure shows that the antibody (sAb) is unable to recognize the modified estradiol (Es-M) (this inability is represented by the cross); however, when HF is present, Es-M is converted into native estradiol (Es) which can then be recognized by the first antibody (sAb). The presence of HF can therefore be detected. The quantity of tracer (gAb+label) bound to the antibody (sAb) is in this case proportional to the quantity of desilylated estradiol which is present in the sample.

The inventors have determined the operating conditions which are advantageous for implementing the method of the present invention, whichever embodiment of the invention is employed. These conditions can naturally be adapted or modified, if necessary, for other silyl groups employed, for other silylated organic compounds or for other means of detection within the meaning of the present invention. These conditions are particularly advantageous for the second embodiment of the present invention.

Thus, the step of bringing into contact in the method of the invention can advantageously be effected at a temperature of from 54 to 64° C. This is because phenomena involving the spontaneous desilylation of the silylated organic compound can appear at temperatures which are too high. The skilled person will be able, without difficulty, to adapt the temperature at which the method of the invention is implemented in dependence on the organic compound and the detection method which are selected.

Also advantageously, the bringing into contact in the method of the invention can be effected at a pH of 4.5 to 6.5, preferably at a pH of 5.5, for example in a 50 mM phosphate buffer or using any appropriate buffer.

This is because phenomena involving the spontaneous desilylation of the silylated organic compound can appear at pH values which are too acid. In this case, too, the skilled person will be able, without difficulty, to adapt the pH at which the method of the invention is implemented in dependence on the organic compound and the detection method which are selected.

According to the invention, the concentration of the silylated organic compound, for example such as estradiol or another compound of equivalent molecular weight, in the measurement solution can be adapted in dependence on the molecular weight of the organic compound and on the detection and/or measurement means employed. In general, the concentration can be from 1 to 2000 ng/ml when the method of the invention is implemented, for example from 2 to 500 ng/ml.

The present invention also relates to a kit for implementing the method of the invention, with said kit comprising the following reagents: a silylated organic compound which is desilylated when it is in the presence of fluorine or hydrofluoric acid; and a means for detecting, in aqueous solution, the appearance of the desilylated organic compound or the disappearance of the silylated organic compound.

The silylated organic compound which is desilylated when it is in the presence of fluorine or hydrofluoric acid is as defined herein.

The means for detecting and/or measuring the appearance of the desilylated organic compound, or the disappearance of the silylated organic compound, in aqueous solution naturally depends on the detection and/or measurement method which is used for implementing the method of the invention. The methods which can be used are as defined above. The detection and/or measurement means can therefore comprise one or more of the following components: colored indicators, markers such as those mentioned above, enzymes, measurement means such as those mentioned above, antibodies which are required for detecting and/or measuring the silylated and/or unsilylated organic compound(s), etc.

For example, the kit can comprise reagents and antibodies which are required for implementing an immunoassay of the competitive type, or reagents and antibodies which are required for implementing an immunoassay of the non-competitive type. The kit can comprise one or more antibodies, for example mouse antibodies, which is/are directed against the unsilylated or desilylated organic compound or against the silylated organic compound. It can additionally comprise one or more antibod(ies), for example goat or rabbit antibodies, which is/are directed against the abovementioned antibodies. It can also comprise a tracer which makes it possible to demonstrate the immunological reaction which has been implemented.

According to the invention, the kit can additionally comprise a support for receiving the reagents, for example a polystyrene strip in which one or more wells have been formed, with this/these well(s) being used as (a) receptacle(s) for the step of bringing into contact, and/or detection and/or measurement, of the method of the invention. Thus, the measurement and/or the detection can readily be effected in wells of microtitration plates. On such a support, for example the abovementioned strip, the wells can be coated with antibody, for example goat or rabbit antibodies, which are directed against the mouse anti-estradiol antibodies. The silylated estradiol can also be bound to the bottom of the wells.

As a result of the present invention, the inventors have succeeded in developing a practical and rapid test for detecting HF at concentrations which can be of the order of 0.001 µg/ml in solution.

The sensitivity of the method of the invention advantageously makes it possible to envisage any industrial application and, in particular, the measurement of atmospheric hydrofluoric acid, which is the most useful. In this case, $1\times10^{-2}$ l of HF/$10^6$ l of air (10 ppb) can easily be detected. The performance of this method is therefore superior to that of the field assays of the prior art, which were limited to detecting HF at concentrations of the order of some hundreds of ppb.

In general, the present invention makes it possible to obtain a result in approximately ½ to 4 hours, depending on the nature of the sample and the detection means employed. Even if some of the times taken are longer than those for certain methods of the prior art, the method of the invention is generally more sensitive.

The method of the invention advantageously applies to any samples containing hydrofluoric acid or fluoride ions: atmospheric sample, foodstuffs, plants and biological media. In each case, the conditions for sampling and for preparing a sample are the same as those of any other method for assaying hydrofluoric acid or fluoride ions.

Another advantage of the present invention is that it is simple to carry out. For example, the technology can be identical to that of immunoassays: employment of ready-to-use reagents, easy-to-handle dispensing, compactness, easy transport and relocation, possibility of working without the provision of energy, and reading with the naked eye or by means of colorimetry using a simple pocket spectrophotometer.

Other applications and advantages of the present invention will also become apparent from reading the description which follows and which is given by way of illustration, and in a non-limiting manner, with reference to the appended figures.

BRIEF DESCRIPTION OF THE FIGURES

FIG. 10 depicts the signal (S) (mOD) obtained for the coupling of estradiol carboxymethyl ether (EstCME) to microtitration plates possessing amino groups (aminated Nunc plates) in dependence on the concentration of the estradiol (in µg/ml).

FIGS. 11 and 12 depict the signal (S) (mOD) (absorbance measured at 414 nm) obtained for the coupling of estradiol carboxymethyl ether to polylysine (poly-Lys)-activated microtitration plates in dependence on the concentration of polylysine (in µg/ml).

FIG. 13 depicts a test of the silylation of estradiol carboxymethyl ether by MTSBTFA: the efficacy of the silylation is measured by the increase in the signal (S) (mOD), in dependence on the dilution of the MTSBTFA (1/5; 1/2; 1/1) and on the temperature in degrees Celsius (° C.).

FIG. 14 depicts an immunometric format test following silylation of the estradiol carboxymethyl ether: the signal (S) (mOD) is measured in dependence on the presence or absence of HF. In this figure Bo represents the signal in the absence of HF (control).

EXAMPLES

Figure 1:
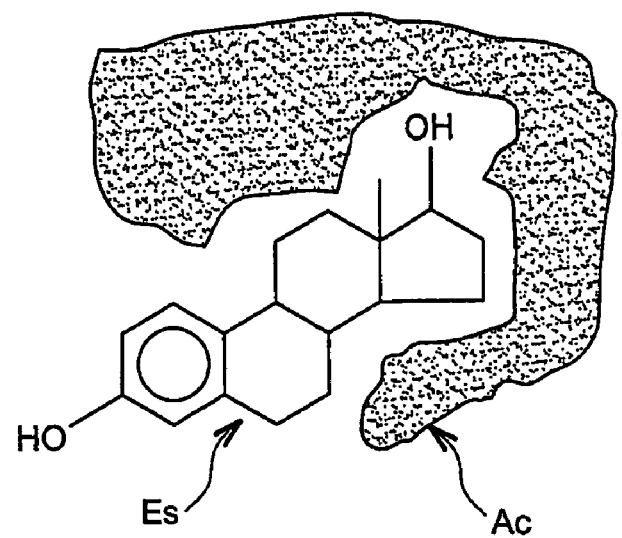
FIG. 1 is a diagram showing the part of the estradiol (Es) molecule which is recognized by its antibody (Ab). The attachment of an Si atom to the —OH of the part of the estradiol molecule recognized by the antibody prevents the antibody from recognizing this molecule.
Figure 2:
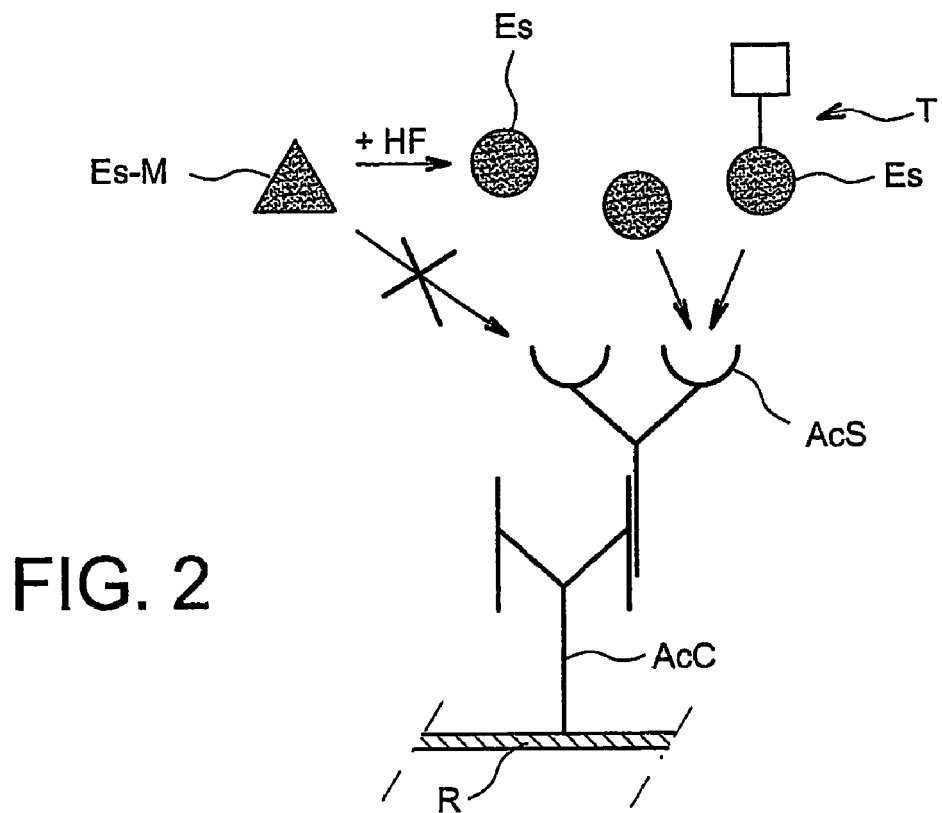
FIG. 2 is a general scheme for detecting HF by means of the method of the invention in accordance with the first embodiment, in which the detection is effected by competition.
Figure 3:
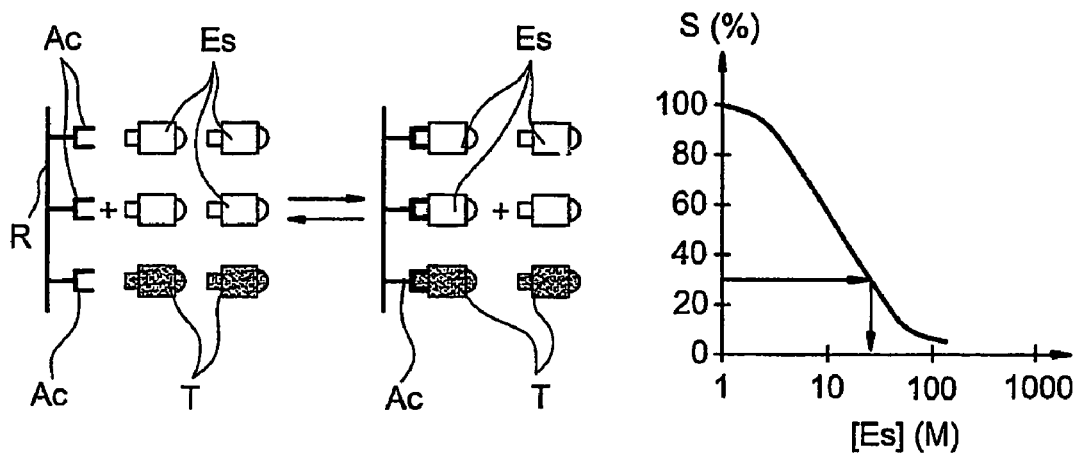
FIG. 3 is a diagram of a competitive immunoassay (on the left) and of the measurement of the signal which is obtained using such an assay (on the right). In this figure, S(%) represents the signal emitted by the tracer (T) which is bound to the antibody (Ab); and [Es] (M) represents the molar concentration (mol/l) of the native estradiol.

The different aspects of the method of the invention has been studied below: the setting-up of the immunological assay for estradiol, tests of the conditions for modifying the estradiol by silylation, verification of the silylated organic compounds by mass spectrometry, testing of the reaction of the silylated compounds with HF, optimization of the chemical nature of the silylated derivatives, optimization of the concentrations of reagents, sensitization of the measurement, optimization of the specificity of the measurement in regard to acids, testing of the applicability of the measurement. The main results of these studies are set out below.

The tests were carried out on samples of atmospheric hydrofluoric acid (simulation in the laboratory) and on samples of water containing fluoride ions.

In order to determine the power of the method of the invention, the inventors defined its sensitivity parameters. Its sensitivity represents the quantity of HF which is required in order to engender a signal which is statistically different from the signal which is obtained in the absence of HF. In accordance with the method of the invention, the quantity of native (unsilylated) estradiol which is present in the sample to be measured depends on the quantity of fluorine which is to convert undetectable silylated estradiol into detectable unsilylated estradiol. For the purpose of measuring HF, therefore, the sensitivity was defined as the requisite quantity of fluorine which, when brought into the presence of dimethyl tert-butyl estradiol, is able to induce a signficant decrease in the bond between the antibody and the enzymic tracer.

Example 1

Application of the Method of the Invention to the Detection and Measurement of the Fluorine by Competitive Immunoassay In this example, the organic compounds which are selected are compounds which are derivatives of β17-estradiol.

1) Preparing the Anti-Estradiol Antibody

The antibody which was used in the assay was produced, in particular, from compounds which were derived from β17-estradiol and which were coupled to bovine albumin with the aim of obtaining antibodies in mice.

The technique employed is that described in reference [39].

2) Preparing an Antibody Mouse Antibody from the Anti-Estradiol Antibody

Goat anti-mouse antibody antibodies marketed by the Immunotech company (Lumigny) are used for coating (dilution at which used: 5 µg/ml) 96-well polystyrene microtitration plates (Nunc). After having been coated, the plates are stored at 4° C. in a buffer containing 0.5% albumin.

Binding to the plate is effected by simple absorption. The incubation should be sufficiently long to enable the protein to become attached. This preparation forms part of the general knowledge of the skilled person.

3) Preparing the Enzymic Tracer

The enzymic tracer was obtained by coupling estradiol to acetylcholine esterase (AChE). Thiol groups are introduced into the estradiol using N-succinimidyl S-acetylthioacetate. The estradiol which has thus been modified is coupled to the AChE, into which maleimide groups which react with the estradiol thiol groups have been introduced. The tracer was purified by gel filtration and then stored in aliquot form at −20° C.

The documents with the reference numbers [44] and [45] describe the techniques and the enzymic tracers which are used for this preparation, and which can be used generally in the present invention.

4) Products and Other Reagents

Estradiol was obtained from Sigma Aldrich. The silylating agents were obtained from the Perbio company.

Hydrofluoric acid is obtained from the Merck-Eurolab company.

All the reagents, i.e. tracer, antibody, estradiol and samples, were used while being diluted in an 0.05M phosphate buffer, pH 7, containing azide (0.01% w/v) (% w/v=ratio of weight in g to a volume of 100 ml) (that is, in this case, 0.01 g/100 ml), bovine alumin (0.5% w/v) and NaCl (0.9% w/v).

5) Optimization of the Silylated Estradiol Concentration Employed

The concentration of silylated estradiol brought into contact with the sample containing HF was optimized in order to enable desilylated estradiol, and therefore the fluorine, to be detected subsequently.

Thus, if the concentration of silylated estradiol employed is very low, this low concentration does not always enable detection to be effected with great precision even if all the silylated estradiol is transformed into estradiol.

A number of tests were carried out in order to determine the optimum concentration of modified estradiol to be used for the desilylation in the method of the invention. This concentration naturally varies in dependence on the reagents employed and on the operational conditions.

In the examples which are presented here, the concentration is preferably 200 ng/ml.

It is possible to estimate that this concentration will in general, in the case of estradiol and its derivatives, be from 1 to 2000 ng/ml, preferably from 2 to 500 ng/ml, with these ranges being given only as an indication, particularly for the conditions of the example.

6) Silylating the Estradiol

One volume of estradiol (2 mg/ml) is mixed with 4 volumes of MTBSTFA and the whole is incubated at room temperature for from 30 minutes to 1 hour.

The silylating agents employed are BTSFA or MTBSTFA. The products which can be obtained are depicted above.

Verification by liquid chromatography and mass spectrometry showed that the estradiol had been silylated.

Having once been silylated, the estradiol is diluted by a factor of 1000 in 100% dimethylformamide (DMF), or else in 100% dimethyl sulfoxide (DMSO), before use.

7) Desilylating the Estradiol 2.5 µl of 1M phosphate buffer (pH=5.5) and 47.5 µl of sample, or of an HF solution of known concentration (standard series), are added to 50 µl of silylated estradiol.

The mixture is shaken and then left at 55-66° C. for 1 hour to dryness in a water bath.

The desilylation reaction can be stopped by diluting the mixture in an assay buffer (dilution by a factor of 40) which is 0.05 M phosphate buffer, pH 7, containing azide (0.01% w/v) (% w/v=ratio of weight in g to a volume of 100 ml) (that is, in this case, 0.01 g/100 ml), bovine albumin (0.5% w/v) and NaCl (0.9% w/v).

8) Enzymic Indicator: Measuring the Enzymic Activity of Acetylcholine Esterase (Ellman Reaction)

The method uses a pseudosubstrate, i.e. acetylthiocholine (AcTCh), which is hydrolyzed at the same rate as acetylcholine. This hydrolysis leads to the formation of thiocholine (TCh), which is able to reduce dithionitrobenzene (DTNB). The reduced DTNB strongly absorbs in the visible range ($\epsilon_{m\ 412\ nm}$=13600 mol$^{-1}$.cm$^{-1}$.l), producing a yellow color.

The AcTCh is used at a concentration at which the activity of the AChE is maximal, taking into account its inhibition by excess substrate. In addition, the quantity of DTNB employed is less than that of AcTCh so as to avoid colorimetric measurements after all the substrate has been transformed. By contrast, the quantity of DTNB employed is in excess as compared to the quantity of TCh produced so as to ensure that the hydrolysis of one molecule of AcTCh leads to the formation of only one molecule of reduced DTNB.

The skilled person knows how to carry out the Ellman reaction and can, on the basis of the information which is provided here, without difficulty find the operational conditions which are optimal for implementing the invention.

9) Immunoassaying the Native Estradiol: Quantifying HF

The estradiol extracts which have previously been obtained are diluted 1/40 and portioned out on assay plates in the presence of the tracer and the anti-estradiol antibodies. The reaction volume is 200 μl.

The immunological reaction is carried out at ambient temperature for one hour.

The assay plates are washed in order to remove unbound tracer and 0.2 ml volumes of indicator solution are added.

After approximately 1 h, the yellow color appears and optical density measurements are carried out using a spectrophotometer.

10) Interpreting the Results

Using a standard HF series, it was possible to determine the concentration of the fluorine contained in the samples in the assays which were performed, thus demonstrating the feasibility of the method of the invention.

Example 2

Study of the Difference in the Specificity of HF Detection in the Case of MTBSTFA-Modified Estradiol and in the Case of BTSFA-Modified Estradiol In all the manipulations described below, the silylated estradiol was used, during the desilylation, at a concentration which was the same for all the samples in a given experiment. This concentration was 200 ng/ml.

In the case of the other reagents, the concentrations were as follows:
 mouse anti-estradiol antibody: 5 μg/ml;
 acetylthiocholine: 7×10$^{-4}$ M;
 5-5'-dithiobisnitrobenzoate: 7×10$^{-4}$ M; and
 estradiol coupled to acetylthiocholine: approximately 1 ng/ml.

The tests were carried out in 300-μl wells on polystyrene strips in the manner explained in Example 1.

Figure 4:
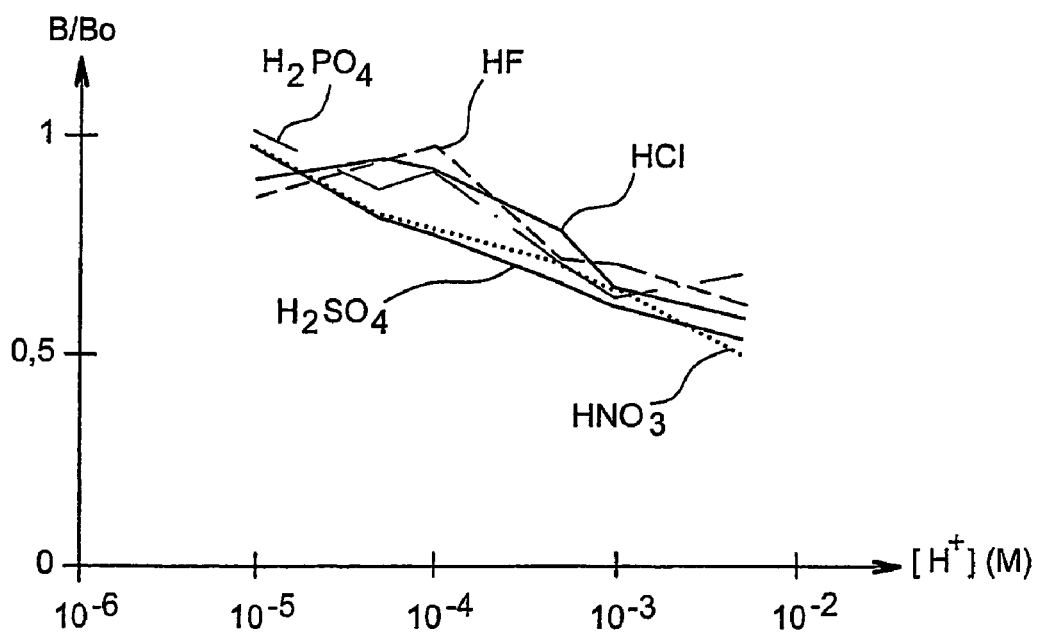
FIG. 4 is a graph which shows the effect of different organic acids on the desilylation of trimethylsilylestradiol which is obtained using BTSFA (B/Bo is a measure of the signal in the form of a ratio between the signal in the presence of HF (B for bound) and the signal in the absence of HF (Bo for unbound) in an immunological test in accordance with the protocol of Example 2 below. [H$^+$] (M) represents the molar concentration of acid for each acid identified in this graph.

A) The estradiol which is silylated with BTSFA (which transfers a trimethylsilyl group) is cleaved (desilylation reaction) with HF, thereby recovering its native form. Such a cleavage can also be observed when using other acids: hydrochloric acid (HCl), nitric acid (HNO$_3$), sulfuric acid (H$_2$SO$_4$) and phoshoric acid (H$_2$PO$_4$). The results are presented in the appended FIG. 4.

Therefore, when this silyl group is used, the desilylation reaction is not always specific for the fluorine. This silylated estradiol is therefore suitable, instead, for detecting HF when the latter is on its own or else for detecting HF when the other acids are not present.

B) Although exhibiting a lower solubility in aqueous medium, the estradiol which is silylated with MTBSTFA (which transfers a silyl group which is more hydrophobic than that transferred by BTSFA) is cleaved (desilylation reaction) specifically by HF, thereby recovering its native form. Thus, as the appended FIG. 6, which was produced under the same conditions, shows, the other acids which were tested do not cleave estradiol which has been modified in this way (see Example 3 below).

The inventors therefore selected MTBSTFA for silylating the estradiol in the examples which follow.

Example 3

Seeking Buffers which are Suitable for the Fluorine Desilylation Reaction in the Method of the Invention Since some acid entities also have an effect on the desilylation of estradiol which has been modified using MTBSTFA (see Example 2), the inventors decided to seek buffer solutions which accentuated the specific effect of the fluorine on the desilylation reaction and inhibited the non-specific effect due to the acid nature of the other compounds which might be present.

When present at high concentrations (necessary for buffering the high acid concentrations), bases such as sodium hydroxide (NaOH) and potassium hydroxide (KOH) also induce desilylation of the estradiol in the absence of acid (data not shown). They cannot, therefore, be used.

Phosphate buffer (KH$_2$PO$_4$/K$_2$HPO$_4$) solutions which were 50 mM in phosphate ion were also tested. They gave good results. The pH of these solutions was studied in order to ensure that their acidity did not result in the silylated estradiol being spontaneously desilylated.

The method of the invention can therefore advantageously be carried out in a buffered medium, for example when the sample may contain other acids or bases which are able to induce spontaneous desilylation of the organic compound and therefore reduce the detection and/or measurement sensitivity of the method of the invention.

Furthermore, the inventors observed that, under certain conditions, a desilylation temperature which was too high could result in the modified estradiol being spontaneously desilylated (data not shown). For this reason, each of the different buffering agents was studied at different temperatures.

Figure 5:
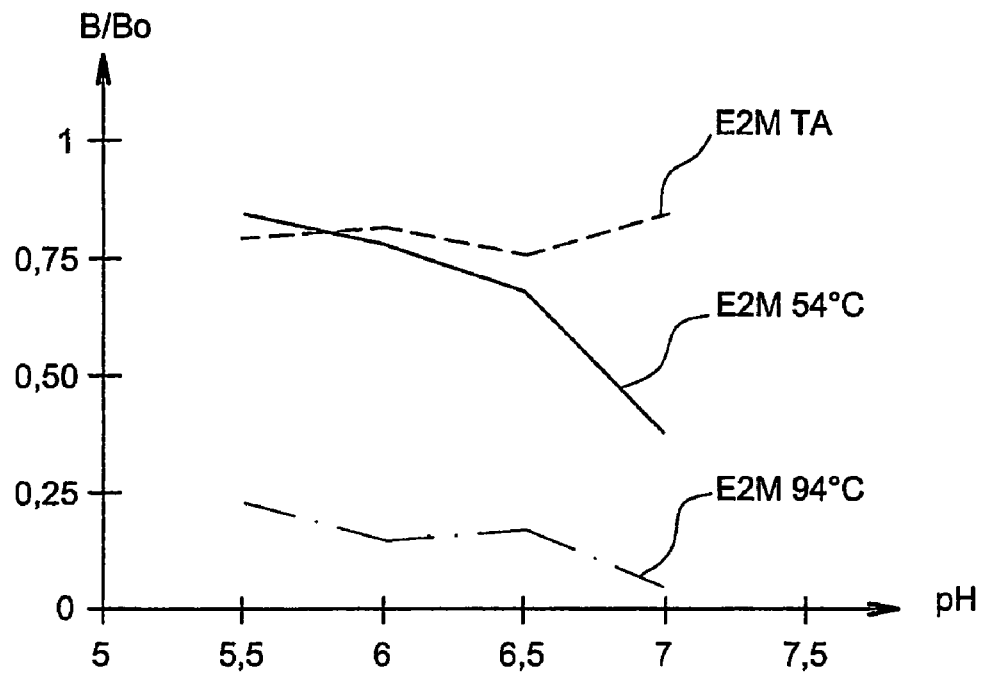
FIG. 5 is a graph which shows a study of the conditions for desilylating estradiol: temperature, and pH of the 50 mM phosphate (P) buffer (the B/Bo signal is measured as in FIG. 4).

The appended FIG. 5 shows the results which were obtained. In this figure "E2M" represents dimethylsilyl tertbutyl estradiol and "A.T." represents the ambient temperature.

While, in the case of phosphate buffer solutions at pH 5.5 or 6, spontaneous desilylation of the silylated estradiol occurs at 94° C., there is no such desilylation at 54° C.

In conclusion, the preferred conditions for desilylating silylated estradiol were set as follows: temperature between 54 and 64° C. in a 50 mM phosphate buffer at pH 5.5. As will be understood, these conditions were determined for estradiol and the abovementioned silyl group, and under the previously mentioned operational conditions.

On the basis of the information which has been provided herein, the skilled person will readily be able to determine other conditions in dependence on the silylated organic compound selected, on the sample and on the conditions under which the method of the invention is implemented.

Example 4

Effect of Different Acids on the Implementation of the Method of the Invention

The effects of various other acids on the desilylation were tested under the conditions mentioned above in Example 3.

Figure 6:
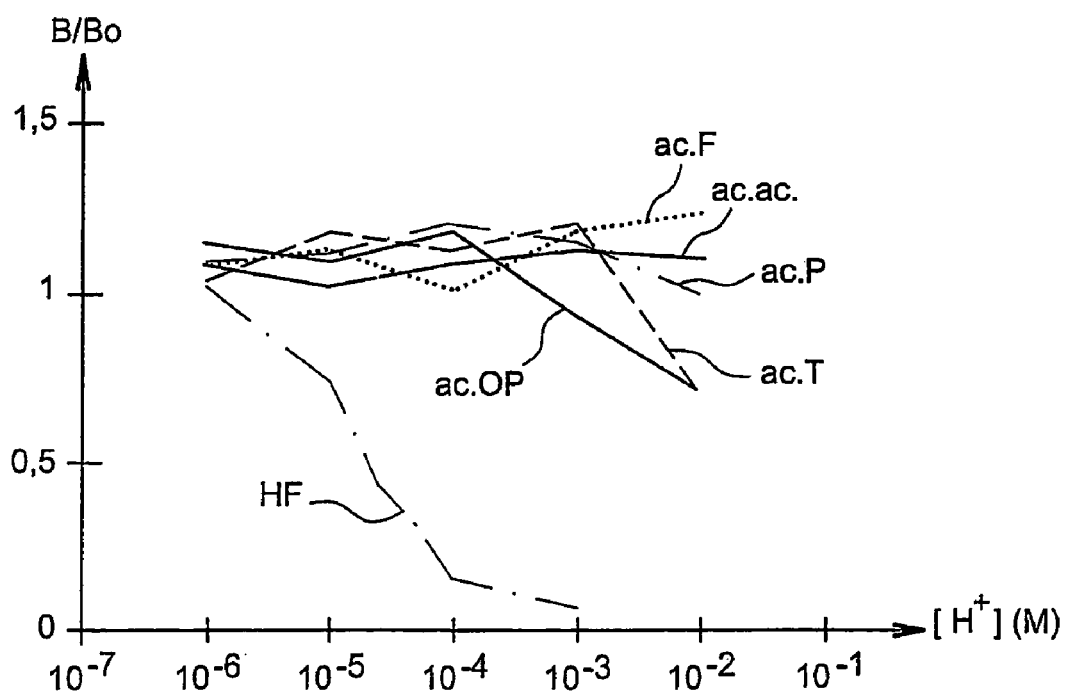
FIG. 6 is a graph which shows the effect of different acids on the desilylation of silylated estradiol in 50 mM phosphate buffer, pH 5.5. [H$^+$] (M) represents the molar concentration of acid for each acid identified in this graph. The data are similar with hydrochloric acid, nitric acid or sulfuric acid (the B/Bo signal is measured as in FIG. 4).

The results of these tests are depicted in FIG. 6. In this figure, "F.ac" represents formic acid; "ac.ac" represents acetic acid; "P.ac" represents phosphoric acid; "OP.ac" represents orthophosphoric acid; and "T.ac" represents trifluoroacetic acid.

These results clearly show that acids other than HF have almost no effect on estradiol which is silylated by MTBSTFA.

The silyl group which is selected therefore plays a role in the specificity of the detection of the fluorine. This fact is to be considered when chemical components other than the fluorine are present in the sample being tested, especially if these components are able to induce desilylation of the organic compound being employed.

Example 5

Specificity for Fluorine as Compared to Other Halogens and Nucleophiles

Fluorine is a halogen and also has a nucleophilic character. In order to test the specificity for fluorine in the estradiol desilylation reaction, the effect of other halogens, such as $Bu_4NBr$, $Bu_4NCl$, $Bu_4NI$ and KI, and of nucleophiles, such as 4-nitrophenol and 4-nitroimidazole, was studied under the operational conditions of the previous examples and with the estradiol being silylated with MTBSTFA.

Figure 7:
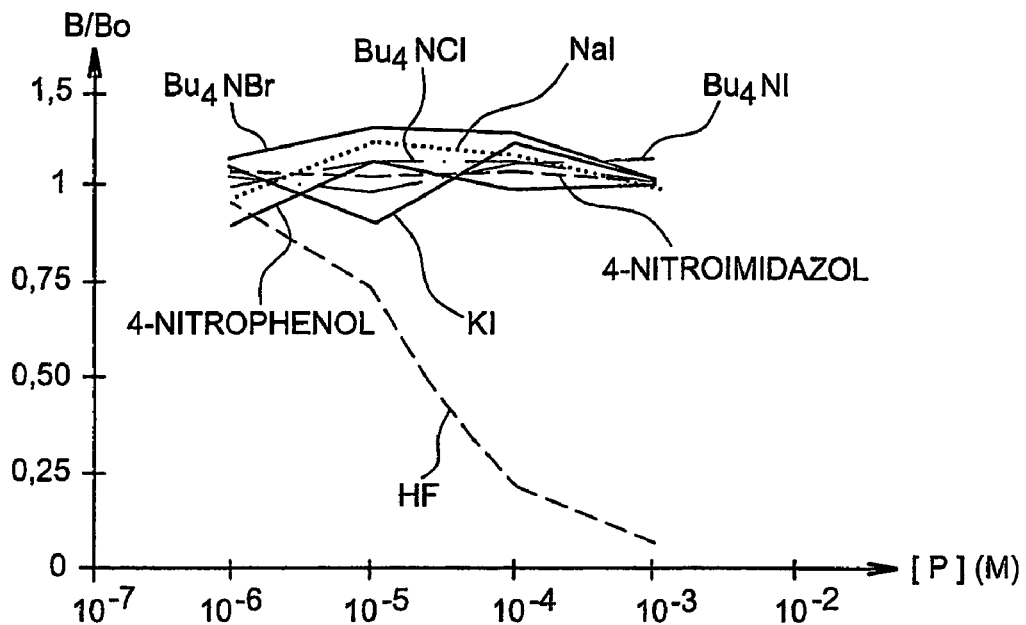
FIG. 7 is a graph which shows the specificity of the detection of HF, as compared to other nucleophiles and halogens, by the method of the invention. [P] (M) represents the molar concentration of halogen or other nucleophiles for each halogen identified in this graph (the B/Bo signal is measured as in FIG. 4).

The appended FIG. 7 depicts the experimental results which were obtained in this example and demonstrates the specific effect of fluorine as compared with other products.

It clearly appears that, in comparison with the other products tested, fluroine is very specific in the estradiol desilylation reaction.

Example 6

Cleavage by HF and by Fluorine Ions

In this example, various fluorine salts were brought into contact with MTBSTFA-silylated estradiol under the experimental conditions used in the preceding examples.

Figure 8:
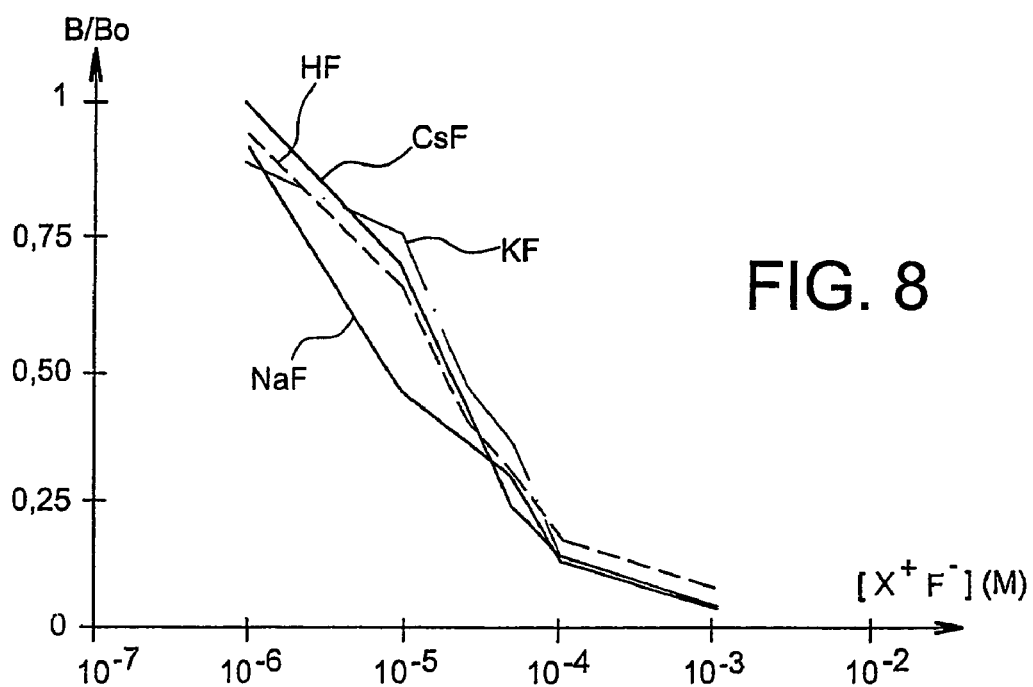
FIG. 8 is a graph which shows the specificity of the detection of HF by the method of the invention in the presence of different salts [X$^+$F$^-$] (M) represents the molar concentration of fluorine salt for each salt identified in this graph (the B/Bo signal is measured as in FIG. 4).

The appended FIG. 8 collates the results which were obtained. In this figure, the usual chemical symbols were used to identify the different fluorine salts which were tested.

The fluorine ions behave similarly to HF in regard to cleaving the silylated estradiol, with this confirming the specificity of the reaction for fluorine.

Example 7

Analytical Power of the Method of the Invention, and Effect of the Addition of an Organic Solvent Under the conditions described in the above examples, the sensitivity for measuring HF is approximately $5 \times 10^{-5}$ M (that is 1 µg/ml) in the case of HF which is diluted in aqueous medium, as FIGS. 7 and 8 show.

During the course of supplementary studies, the inventors noted that the sensitivity of the method of the invention can be increased still further by adding a water-miscible organic solvent to the aqueous desilylation solution.

The experiment was carried out using dimethylformamide (DMF) (see silylation of estradiol) and dimethyl sulfoxide (DMSO).

The sensitivity can be improved by a factor of 500 (approximately $10^{-7}$ M, that is 0.001 µg/ml) by using dimethyl sulfoxide (DMSO) as solvent for implementing the desilylation in accordance with the method of the invention.

Figure 19:
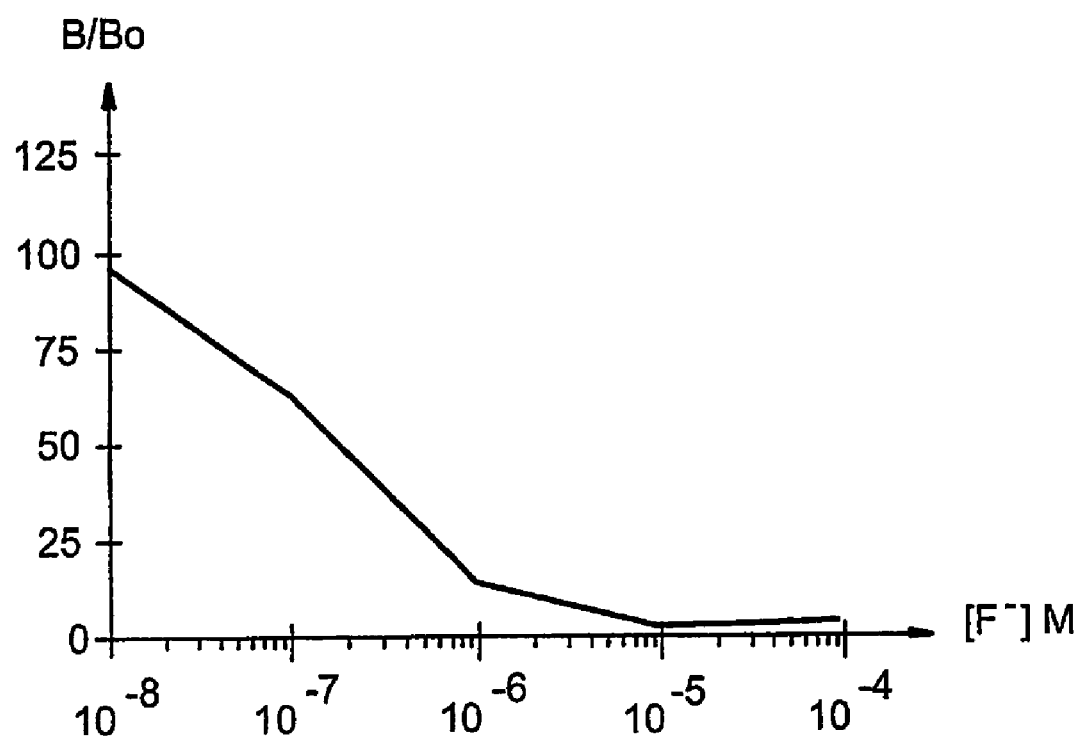
FIG. 19 is a graph which shows the results of detecting the fluorine by the method of the invention in the presence of dimethyl sulfoxide (DMSO): B/Bo is a measure of the signal in the form of a ratio between the signal in the presence of HF (B) and the signal in the absence of HF (Bo), and [F−] (M) is the molar concentration of fluoride ions.

FIG. 19 depicts the dose-response curve for fluoride ions in the case of a reaction carried out in the presence of dimethyl sulfoxide at a concentration of 95% by volume based on the total volume of the contacting aqueous solution. These results are to be compared with those from the previous examples.

The addition of the organic solvent to said contacting aqueous solution therefore substantially increases the sensitivity for detecting and/or measuring fluorine by the method of the invention.

Example 8

Using the Method of the Invention when the Compound of the Invention is an Estradiol Derivative In this example, the organic compound employed for implementing the method of the invention is an O-methyl derivative of estradiol ($E2OCH_3$): 17-betaestradiol 3-methyl ether of the formula:

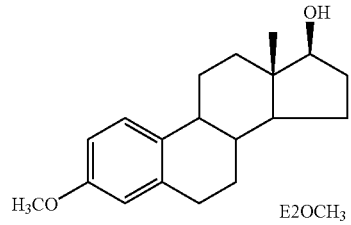

The operational conditions which are used are those explained in Examples 1 and 2 above.

Figure 17:
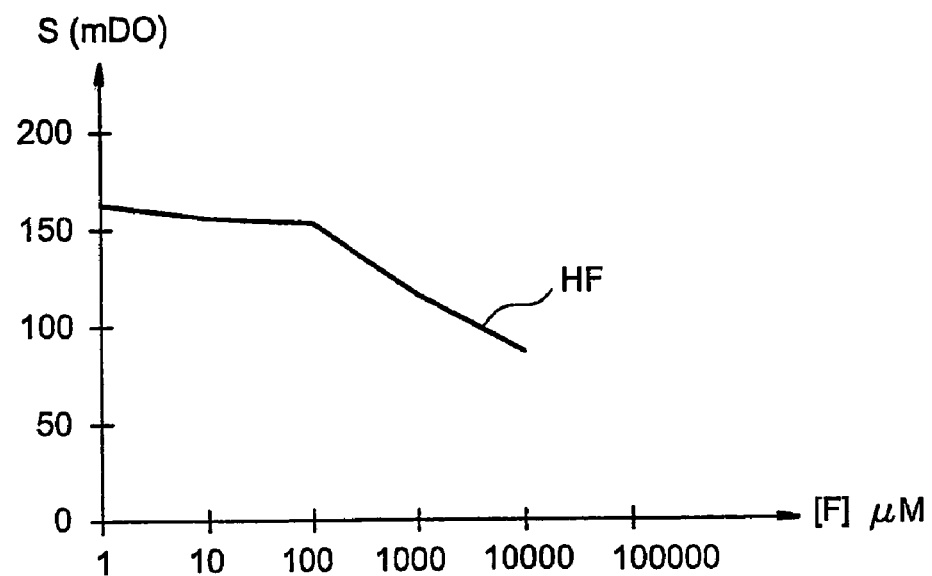
FIG. 17 depicts, in the form of a graph, experimental results obtained from implementing the method of the invention using a silylated organic compound which is a derivative of estradiol: the signal (S(mOD)) is measured at 414 nm in dependence on the concentration of fluorine [F] in micromoles/l (µM).
Figure 18:
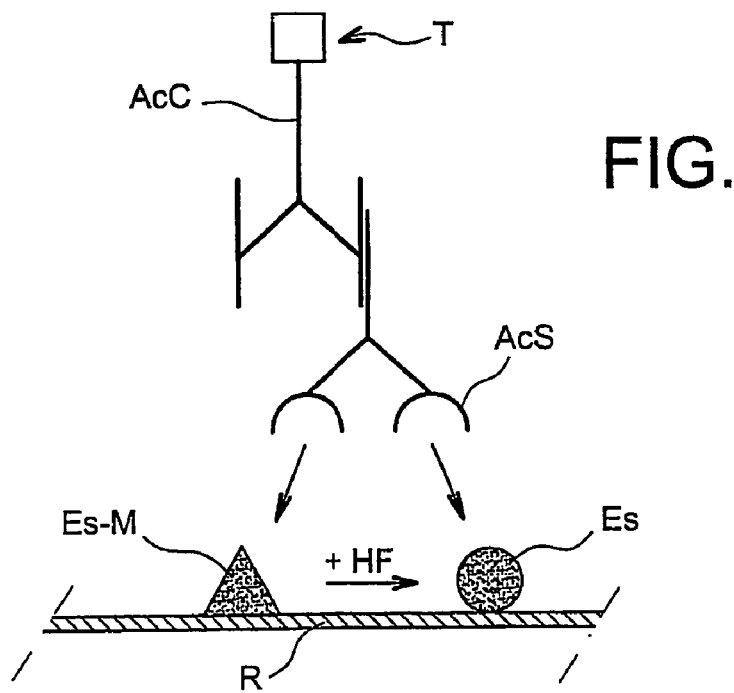
FIG. 18 diagrammatically depicts the mechanism of a non-competitive immunological detection as can be used in the detection step of the method of the invention.

The experimental results which are obtained are reported in the appended FIG. 17. It is indeed observed that $E2OCH_3$ is desilylated in the presence of fluorine.

There are, therefore, cogent reasons for using an estradiol derivative in the method of the invention.

Example 9

Using the Method of the Invention when the Organic Compound is a Peptide Possessing Hydroxyl Functions In this example, the organic compound is a peptide. The peptide is a tetrapeptide, i.e. acetylated Ser-Asp-Lys-Pro (AcSDKP) of the formula:

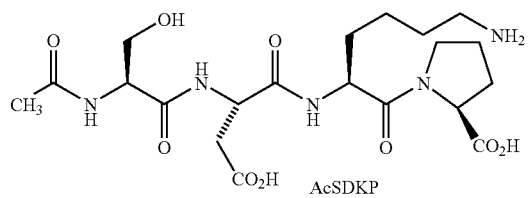

AcSDKP is a peptide which possesses hydroxyl groups, advantageously allowing it, at one and the same time, to be silylated and to be attached to a solid phase by its carboxyl or amino groups.

The silylation reactions of this peptide were studied first of all, with this being followed by a study of the use of this silylated compound in the method of the invention.

AcSDKP (1 mg/ml) was silylated with undiluted BSTFA or MTBSTFA for 10, 30 or 60 minutes at 22° C., 37° C. or 60° C. After the reaction, the silylated AcSDKP was detected by an AcSDKP-specific competitive assay by means of the technique described in document [5] and using rabbit polyclonal antibodies. In this case, an increase in the signal indicates that immunoreactivity has been lost and that the silylation has therefore been effective.

Figure 15:
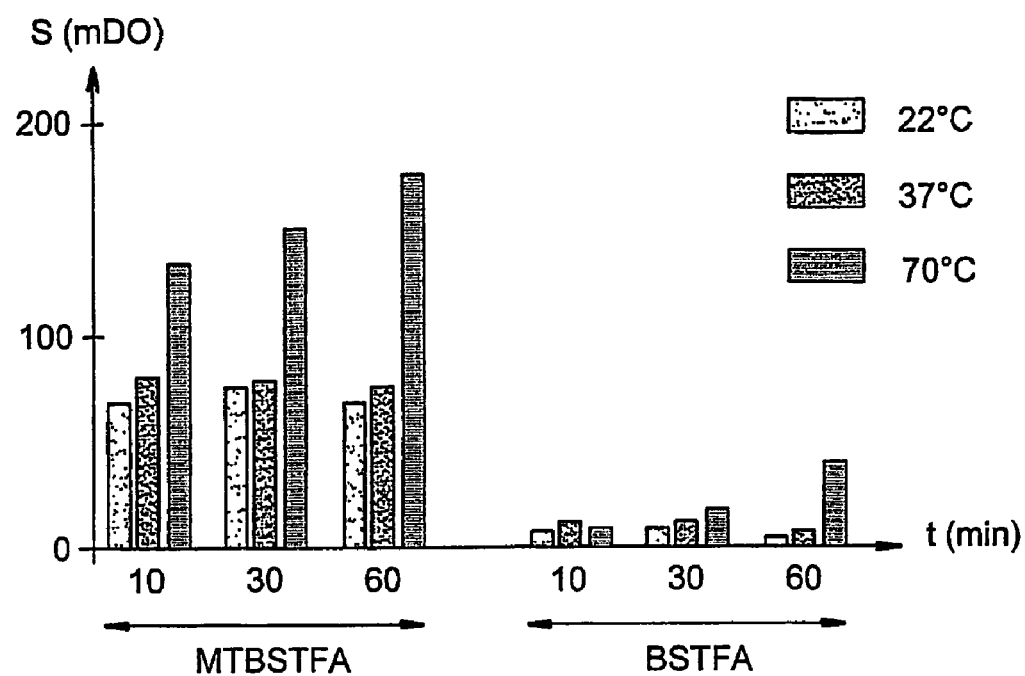
FIG. 15 depicts, in the form of a graph, experimental results obtained from implementing the method of the invention using a silylated organic compound which is a tetrapeptide, AcSDKP: the signal (S(mOD)) is measured at 414 nm. Two series of assays were carried out: one series using the tetrapeptide which was silylated with a first silylating reagent (MTSBTFA), and one series using the tetrapeptide which was silylated with a second silylating reagent (BSTFA). Three assays were carried out in each series: at 22° C., at 37° C. and at 70° C., and measurements were made at 10, 30 and 60 minutes in each case.

As the appended FIG. 15, which reports the experimental results obtained, shows, MTSBTFA decreases the reactivity of the AcSDKP at 60° C., with this suggesting that the compound has been silylated.

Figure 16:
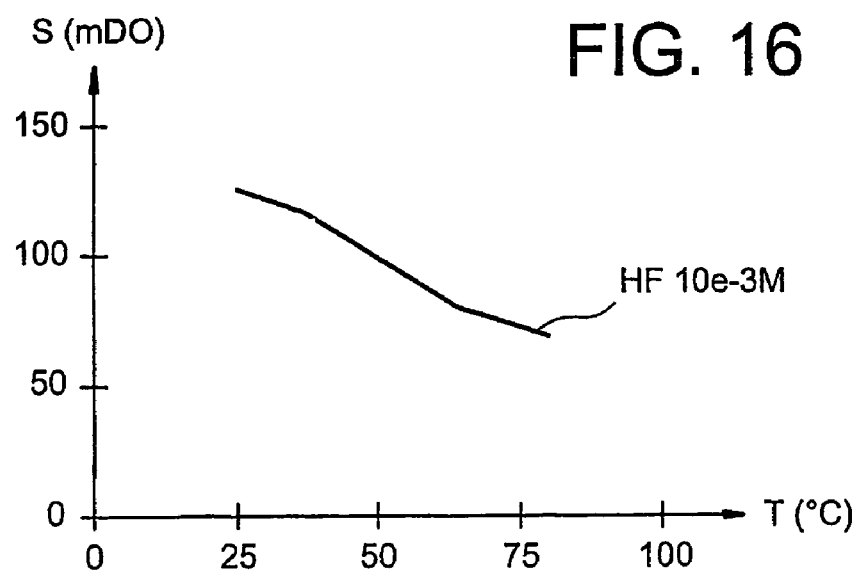
FIG. 16 is a graphic depiction of experimental results which were obtained in a study of the efficacy of the detection of the fluorine by the method of the present invention in dependence on the desilylation temperature (T(° C.)): the signal (S(mOD)) is measured at 414 nm. The silylated compound employed is that of FIG. 15 obtained with MTBSTFA.

Desilylation tests were then carried out on this silylated peptide in the presence of HF, in accordance with the present invention. The appended FIG. 16 collates the results which were obtained. It is seen that the HF desilylates the peptide. Thus, the loss of the silylated group results in immunoreactivity being increased and therefore in the signal becoming weaker. As the figure shows, the signal decreases in the presence of HF.

The method of the invention can therefore be implemented when using a hydroxylated peptide as the organic compound.

Example 10

Detecting and Measuring Fluorine in Solution

In order to verify the validity of the method of the invention, the authors tested various mineral waters whose concentration of fluorine is known.

The protocol employed is that of Example 1 and the organic compound selected is estradiol silylated with MTBSTFA (dimethyl tert-butyl estradiol).

Table I below collates the results which were obtained in this example. The table shows that the presence of fluorine was detected in every case.

The correlation between the theoretical concentration and the concentration which was found appears correct in the case of the most concentrated water samples. It is possible that the nature of the fluorine present in the sample is the cause of the few variations which were observed.

TABLE I

Measurement of fluorides in mineral waters

| Water samples | [fluorides] mg/ml | μM | [dry extracts] mg/ml | pH | [F] detected μM | % of F found |
|---|---|---|---|---|---|---|
| Vichy St Yorre | 9 | 470 | 4774 | 6.6 | 780 ± 271 | 170 ± 60 |
| San-Pellegrino | 0.61 | 32 | 1074 | 7.5 | 151 | 470 |
| Badoit | 1 | 52 | 1200 | 6 | 28.5 ± 12 | 50 ± 20 |
| Vichy Célestin | 6 | 135 | 3325 | 6.8 | 305 ± 81 | 97 ± 26 |
| Quézac | 2.1 | 100 | — | — | 53 | 53 |

Example 11

Detecting and Measuring Fluorine from Gaseous Media

The HF to be measured is frequently in gaseous form and it is necessary to pass it into aqueous solution in order to measure it. Since they did not have any air which was contaminated with HF, the inventors artificially created such samples by evaporating an HF solution of known concentration in a sealed container. Once the HF had evaporated, the air was pumped into, and caused to bubble in, a collecting buffer (DMF).

Using a system which enables 100 liters of air, whose concentration of HF is $1.2 \times 10^{-2}$ $l/10^6$ l of air (12 ppb), to be filtered, an HF concentration of $10^{-5}$ M is obtained in solution (subject to a 100% yield).

The protocol which is used for detecting the fluorine is that described in Example 1. The organic compound selected is estradiol silylated with MTBSTFA (dimethyl tert-butyl estradiol).

Figure 9:
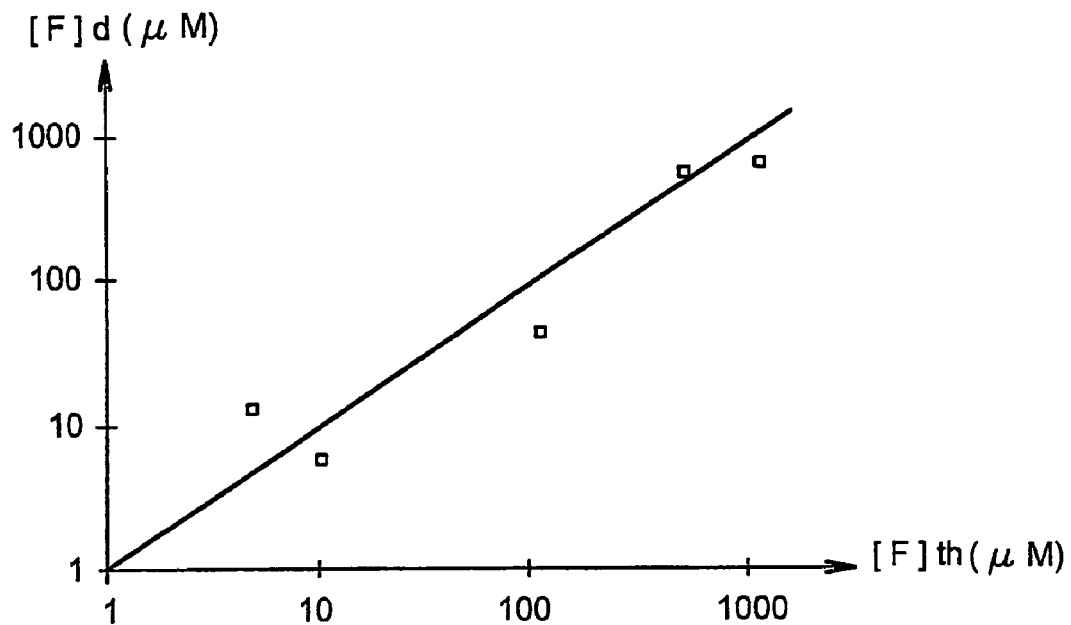
FIG. 9 is a graph which shows the correlation between the concentration of fluorine [F] (in µmol/l) which is detected (d) by the method of the invention and the theoretical concentration ([F]$_{th}$) in samples of atmosphere which is contaminated with fluorine.

The results which are presented in FIG. 9 show that the fluorine is detected in every case. The correlation between the theoretical and detected concentrations of fluorine is fairly good.

The method, according to the invention, for detecting HF in air therefore easily makes it possible to detect HF at concentrations of the order of $10^{-2}$ l of $HF/10^6$ l of air (10 ppb).

Example 12

Applying the Method of the Invention to the Detection and Measurement of Fluorine by Means of Non-Competitive Immunoassay 1) General Strategy The aim is to use the previously acquired results, namely the possibility of modifying the immunological recognition of a silylated compound by the action of HF.

As compared to the previous assay format (competitive), the immunometric approach consists in immobilizing the silylated compound covalently on a solid surface. Its transformation by HF leads to an immunoreactive form, and therefore to the appearance of a signal, contrary to the competitive assay in which the signal disappears.

This format frequently results in superior sensitivity, probably due to favorable thermodynamics linked to the reagents which are in excess and to easier reading, based on the fact that it is easier to see or measure the appearance of a signal than its disappearance.

2) Reagents and Protocol

The antibody employed is that described in reference [39].

The biotinylation of the rabbit antibody and the labeling of the streptavidin or the antibodies with acetylcholine esterase were carried out in the laboratory using the customary techniques known to the skilled person.

All the chemical reagents and products were obtained from Sigma or Merck. The compounds obtained come from Sigma or Steraloids (in the case of the estradiol derivatives).

The assay buffer is an 0.05 M phosphate buffer, pH 7.4, containing azide (0.01%), bovine albumin (0.5%) and NaCl (0.9%).

The enzymic indicator consists of a mixture of acetylthiocholine and dinitrifluorobenzene. Following reaction with the tracer, it produces a yellow color which is visible to the naked eye or which can be quantified using a spectrophotometer at 414 nm.

The plates which were used for carrying out the experiments, in particular for attaching the estradiol derivative, come from Nunc (Rochester, USA).

The silylating agents employed are BSTFA and MTB-STFA.

The estradiol which is used is shown below. The advantage of this compound is that it makes it possible to use antibodies for the detection and the basic principle which was previously developed for the competitive assay.

The inventors firstly verified that the anti-estradiol antibodies which were obtained recognized the unsilylated compound (53% cross-reaction with the antibodies as compared to estradiol) and not the silylated compound. The verification was positive.

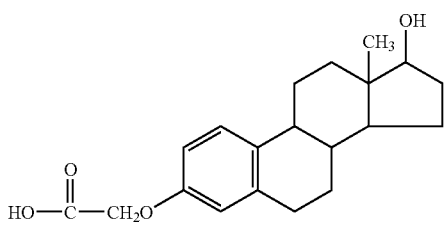

Structure of Estradiol Carboxymethyl Ether (EstCME)

The inventors then tested the covalent attachment (binding) of the estradiol to two types of plate: plates possessing amino groups (Nunc-NH$_2$ plates) and plates which were activated with polylysine (poly-Lys).

3) Tests of the Attachment of the Estradiol Derivative

The EstCME was incubated on Nunc plates in the presence of equimolar concentrations of N-hydroxysuccinimide (NHS), an agent which binds the amino groups on the plate to the carboxyl groups of the antigen, at 22° C. for 3 hours. Visualization was effected using a 100 ng/ml anti-estradiol antibody at 20° C. for 4 hours and then using a goat anti-rabbit antibody antibody coupled to acetylcholine esterase (2 Ellman units of gAb-AchE/ml) at 22° C. for 2 hours. The enzymic activity is visualized by adding the Ellman reagent, a substrate of the AchE.

Figure 10:
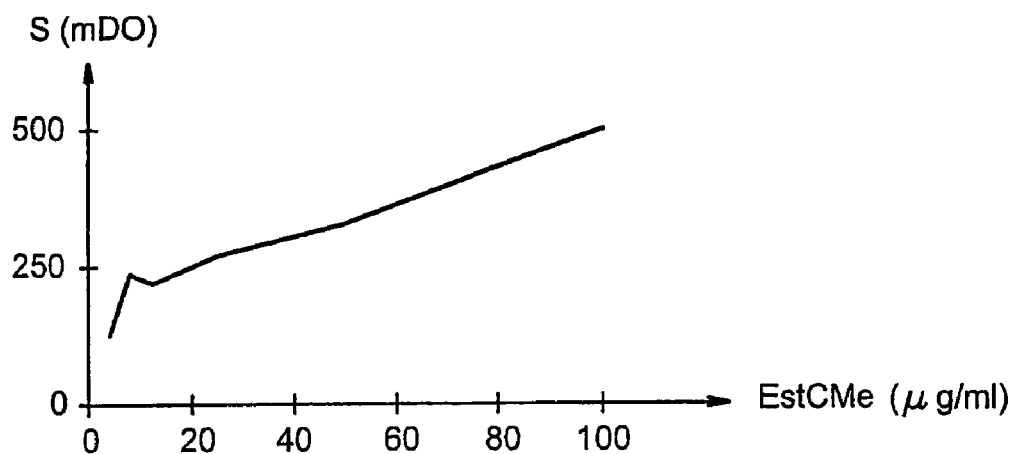
FIGS. 10 to 14 are graphic representations of experimental results obtained in regard to the recognition of unsilylated estradiol by specific antibodies in accordance with non-competitive immunological assay protocols. In these figures.

The results which were obtained are reported in the appended FIG. 10. They show that the estradiol is bound effectively and that the maximum appears to be achieved at the highest concentration tested (100 µl/ml).

This initial experiment was repeated using plates on which polylysine (poly-Lys) (between 1 and 100 µg/ml in phosphate buffer) had previously been absorbed.

Figure 11:
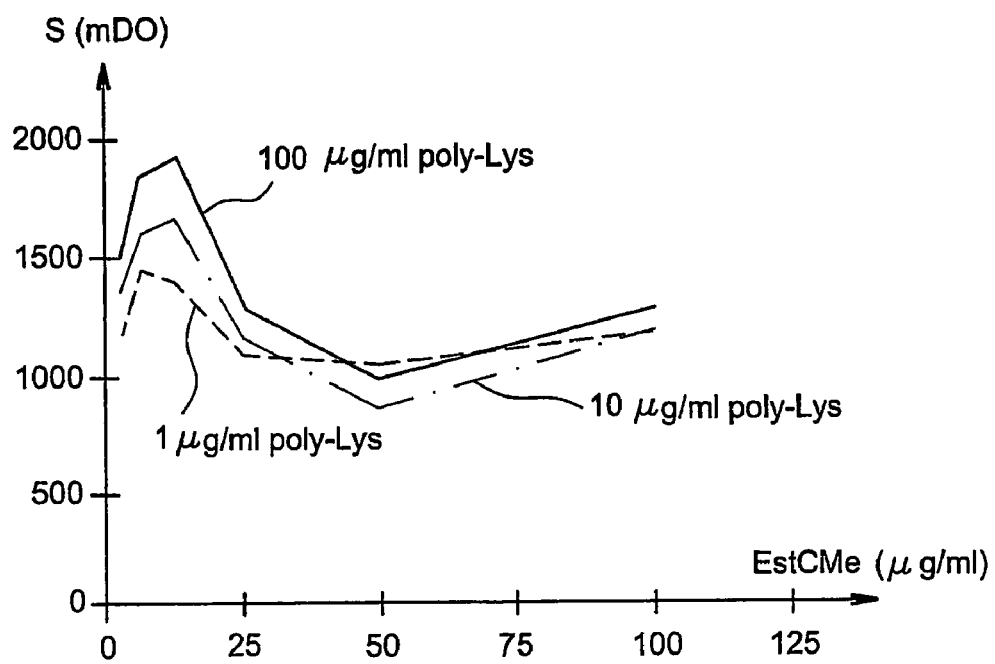

The results which were obtained are reported in the appended FIG. 11. In this case, the results are of the same order whatever the concentration of polylysine studied. This furthermore demonstrates that the amino groups carried by the polylysine are more accessible for binding the chosen estradiol.

Figure 12:
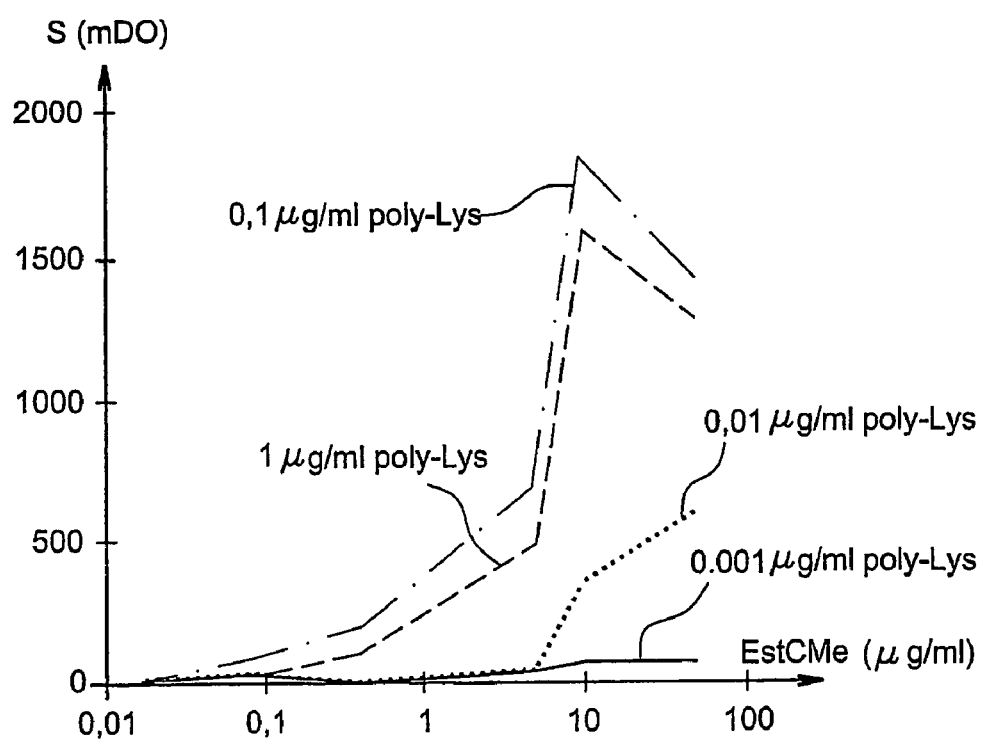

In order to study the influence of the concentration of polylysine in more detail, the test was repeated using a wider range of polylysine concentrations. The results which were obtained are reported in the graph in the appended FIG. 12. They show an optimum for polylysine around 1 µg/ml.

The two preceding figures (FIGS. 11 and 12) appear to indicate effective coupling of the estradiol derivative to the plates, with a plateau obtained at a polylysine concentration of 1 µg/ml and an estradiol carboxymethyl ether concentration of 10 µg/ml.

4) Silylating the Estradiol Derivative

In addition, the inventors sought to demonstrate the best conditions for silylating the above mentioned compound. The estradiol carboxymethyl ether was reacted, for from 0 to 60 minutes, with MTBSTFA at various concentrations (1/5, 1/2 and 1/1) and two temperatures (22° or 37° C.). The silylation is measured by means of the competitive assay of the silylated estradiol in which the silylated estradiol loses its recognition (and in which the signal should increase).

Figure 13:
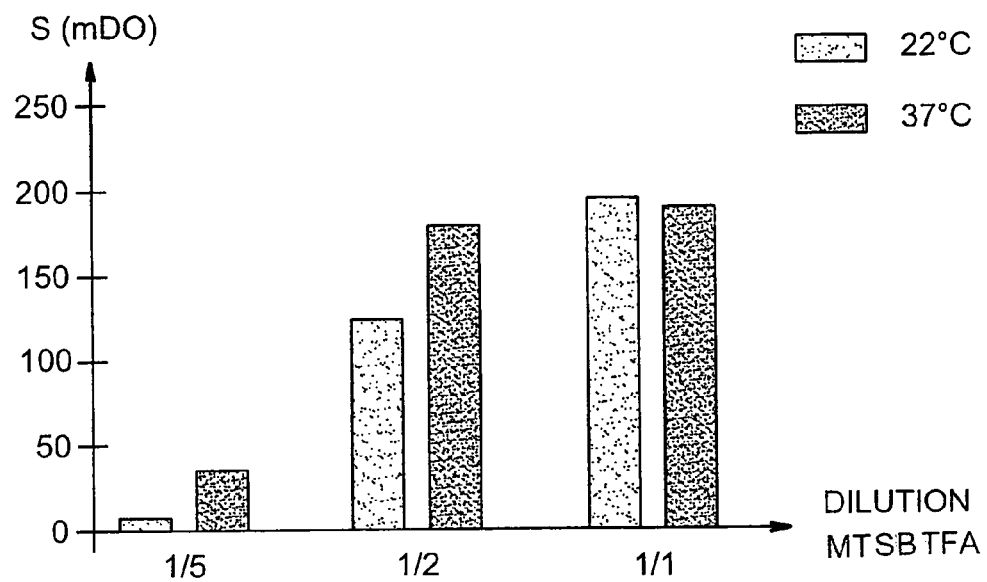

The results which were obtained are reported in the appended FIG. 13. This figure shows that, under conditions of high MTBSFA concentration, the estradiol carboxymethyl ether loses its immunoreactivity. This loss is indicated by an increase in the signal, due to the absence of recognition. The MTBSFA is demonstrated to have a dose effect.

These results taken together, i.e. efficacy of the coupling to the solid phase and of the silylation, enabled the following coupling/desilylation test to be carried out on plates.

5) Coupling/Desilylation Test

The estradiol carboxymethyl ether (8.3 mg/ml) was reacted, at 22° C. for 1 hour, in the presence of MTBSTFA at the same concentration and then diluted in water to 1 µg/ml and reacted, at 22° C. for 1 hour and in the presence of NHS, on plates which were coated with polylysine (1 µg/ml).

Desilylation was effected, at 22, 37 or 64° C. for 1 hour, in the absence or presence of HF at a concentration of 1 mM.

Figure 14:
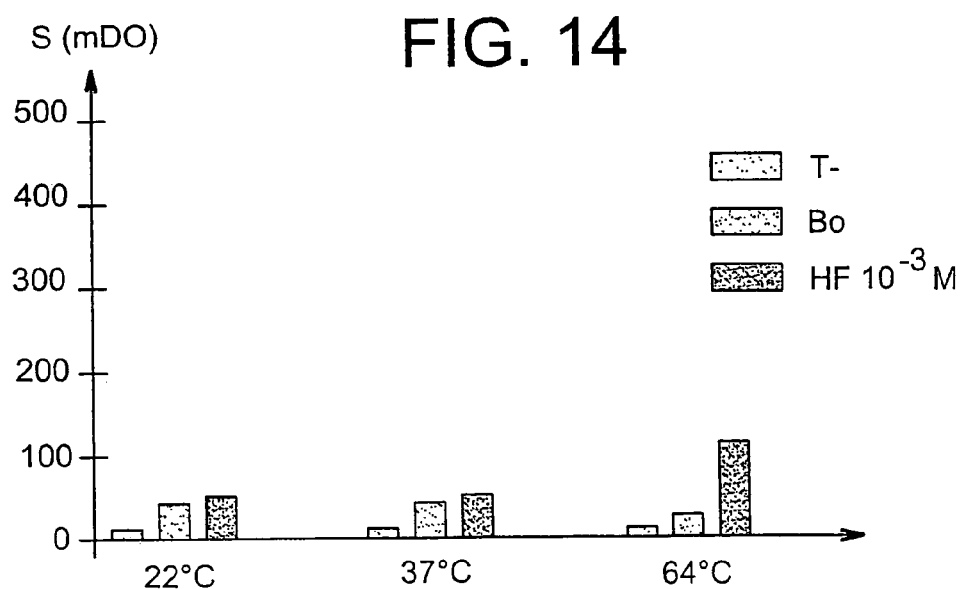

The results are reported in the appended FIG. 14. As this figure shows, it is possible to observe an increase in the immunoreactivity which corresponds to a desilylation of the silylated estradiol carboxymethyl ether in the presence of HF.

This thereby demonstrates the detection of HF by the method of the invention when the silylated organic compound is bound to a support.

REFERENCE LIST

[1] International Society for Fluoride Research, Fluoride 31(2), 1998, 74-80—disponible sur le site Internet http://www.fluoride-journal.com/98-31-2/31274-80.htm.
[2] Occupational Safety and Health Administration", http://www.osha-dlc.gov/dts/sltc/methods/inorganic/id110/id110.html.
[3] Alexei Vasiliev et al, Elsevier, Analytica chimica acta, Sensor and Actuators, B 49 (1998), 133-138.
[4] http://www.bionics-instrument.com/p_fluorine.htm.
[5] Ezan E et al, Pharmcokinetics in healthy volunteers and patients of NAc-SDKP (seraspenide), a negative regulator of hematopoiesis, Drug Metab Dispos 1994 November-December; 22(6):843-848.
[6] Shi R Z et al., Development of an enzyme-linked immunosorbent assay with monoclonal antibody for quantification of homovanillic acid [corrected] in human urine samples, Clin Chem 1998 August; 44(8 Pt 1):1674-1679.
[7] Taran F et al., Competitive enzyme immunoassay for urinary vanillylmandelic acid, Clin Chim Acta 1997 Aug. 29; 264(2):177-192.
[8] Boschelli et al, Tetrahedron Letters 26, 5329-5242, 1985.
[9] Machard S et al., A sensitive amphotericin B immunoassay for pharmacokinetic and distribution studies, Antimicrob Agents Chemother 2000 March; 44(3):546-550.

[10] Cleary J D et al., Amphotericin B enzyme-linked immunosorbent assay, Antimicrob Agents Chemother 1996 March; 40(3):637-641.

[11] Fitzgerald R L, Herold D A., Serum total testosterone: immunoassay compared with negative chemical ionization gas chromatography-mass spectrometry, Clin Chem 1996 May; 42(5):749-755.

[12] Luceri F et al., Gas chromatography-mass spectrometry measurement of 6-beta-OH-cortisol/cortisol ratio in human urine: a specific marker of enzymatic induction, Clin Chem Lab Med 2001 December; 39(12):1234-1249

[13] Munro C J et al., Relationship of serum estradiol and progesterone concentrations to the excretion profiles of their major urinary metabolites as measured by enzyme immunoassay and radioimmunoassay, Clin Chem 1991 June; 37(6):838-844.

[14] Metaye T et al., Comparative measurement of progesterone receptors in breast cancer by biochemical and immunoenzymatic assays, Ann Biol Clin (Paris) 1990; 48(10): 732-736

[15] Foekens J A et al., Comparison of enzyme immunoassay and dextran-coated charcoal techniques for progesterone receptor determination in human breast cancer cytosols, J Steroid Biochem 1988 June; 29(6):571-574.

[16] Hosoda H et al., Sensitivity of steroid enzyme immunoassays. Comparison of four label enzymes in an assay system using a monoclonal anti-steroid antibody, Chem Pharm Bull (Tokyo) 1989 July; 37(7):1834-1837

[17] Hubl W et al., An improved solid-phase enzyme and luminescent immunoassay system for steroid hormones and digoxin, Clin Chem 1988 December; 34(12):2521-2523

[18] Hocart C H et al, Mass spectrometry and chromatography of t-butyldimethylsilyl derivatives of cytokinin bases, Cytokine Anal Biochem 1986 Feb. 15; 153(1):85-96.

[19] Garcia de Salamone I E et al., Cytokinin production by plant growth promoting rhizobacteria and selected mutants, Can J Microbiol 2001 May; 47(5):404-411.

[20] Trione E J et al., A quantitative fluorescence enzyme immunoassay for plant cytokinins, Anal Biochem 1987 April; 162(1):301-308.

[21] Steffenrud S et al., Gas chromatography-mass spectrometry of monohydroxyeicosatetraenoic acids as their methyl esters trimethylsilyl, allyldimethylsilyl and tert.-butyldimethylsilyl ethers, J Chromatogr 1987 May 15; 416(2):219-235.

[22] Smith B J et al, Measurement of plasma prostaglandin E2 using capillary gas chromatography negative ion chemical ionization mass spectrometry, Res Commun Chem Pathol Pharmacol 1983 April; 40(1):73-86.

[23] David Percival M, Continuous spectrophotometric assay amenable to 96-well plate format for prostaglandin E synthase activity, Anal Biochem 2003 Feb. 15; 313(2):307-310.

[24] Hoffman S W et al., A reliable and sensitive enzyme immunoassay method for measuring 8-isoprostaglandin F2 alpha: a marker for lipid peroxidation after experimental brain injury, Neurosci Methods 1996 October; 68(2): 133-136

[25] Knapp R D 1979 Handbook of analytical derivatization reactions New York John Willey and sons.

[26] Lau H L et al, 1966, J Gas Chromatography 4, 136.

[27] Tallent W H, et al., Bis(trimethylsilyl)acetamide in the silylation of lipolysis products for gas-liquid chromatography, J Lipid Res 1968 January; 9(1):146-148

[28] Mawhinney T P et al., Gas-liquid chromatography and mass spectral analysis of mono-, di- and tricarboxylates as their tert.-butyldimethylsilyl derivatives, J Chromatogr 1986 Jun. 27; 361:117-

[29] Mawhinney T P et al., Simultaneous determination of N-acetylglucosamine, N-acetylgalactosamine, N-acetylglucosaminitol and N-acetylgalactosaminitol by gas-liquid chromatography, J Chromatogr 1986 Jan. 3; 351(1):91-102

[30] Bazan A C and Knapp D R, Improved derivative of 6-ketoprostaglandin F1 for gas chromatography-mass spectrometric analysis, J Chromatography 1982, 236, 201-207.

[31] Choi M H et al., Determination of estrone and 17 beta-estradiol in human hair by gas chromatography-mass spectrometry, Analyst 2000 April; 125(4):711-714.

[32] Dehennin L, Estradiol-17 beta determined in plasma by gas chromatography-mass spectrometry with selected ion monitoring of mixed silyl ether-perfluoroacyl ester derivatives and use of various stable-isotope-labeled internal standards, Clin Chem 1989 April; 35(4):532-.

[33] Andersson S H et al., Analysis of profiles of unconjugated steroids in rat testicular tissue by gas chromatography-mass spectrometry, J Steroid Biochem 1985 October; 23(4):469-.

[34] Ishikawa E et al., Development and applications of sensitive enzyme immunoassay for antibodies: a review, J Clin Lab Anal 1989; 3(4):252-265.

[35] Ishikawa E, Development and clinical application of sensitive enzyme immunoassay for macromolecular antigens-a review, Clin Biochem 1987 December; 20(6):375-385.

[36] Oellerich M, Enzyme-immunoassay: a review, J Clin Chem Clin Biochem 1984 December; 22(12): 895-904.

[37] O'Sullivan M J et al., Enzyme immunoassay: a review, Ann Clin Biochem 1979 September; 16(5):221-240.

[38] EZAN E et al, Strategies for developing specific and sensitive radioimmunoassays. In: Handbook of Pharmacology: Radioimmunoassay in basic and clinical pharmacology (Patrono C. and Beskar P., eds) 82(1987)143-179.

[39] Buscarlet L et al., Cross-linking of 17 beta-estradiol to monoclonal antibodies by direct UV irradiation: application to an enzyme immunometric assay, Anal Chem 1999 Mar. 1; 71(5):1002-1008.

[40] Nakagomi M et al., Enzyme immunoassay for the measurement of 17-alpha-estradiol 17-N-acetylglucosaminide in rabbit urine, Steroids 1999 April; 64(4):301-307.

[41] el Jabri J, Enzyme immunoassay for plasma estradiol using a monoclonal antibody, J Steroid Biochem Mol Biol 1991 March; 38(3):339-343.

[42] Dhar T K et al., Homogeneous enzyme immunoassay of estradiol using estradiol-3-O-carboxymethyl ether as hapten, Steroids 1988 May-June; 51(5-6):519-526.

[43] ELLMAN G. L. et al., (1961) Biochem. Pharmacol. 7, 88.

[44] EP-A-0139552.

[45] U.S. Pat. No. 5,047,300.

The invention claimed is:

1. A method for detecting and/or measuring the concentration of fluoride ($F^-$) or hydrogen fluoride (HF) in a sample, comprising contacting, in aqueous solution, said sample with a silylated organic compound in order to obtain a measurement solution, wherein said silylated organic compound being desilylated when it is in the presence of hydrofluoric acid or of fluoride, and wherein the silylated organic compound and the desilylated organic compound being able to be detected and/or measured separately from each other; and detecting and/or measuring, in said measurement solution, the appearance of the desilylated organic compound, or the disappearance of the silylated organic compound, which takes place if fluoride or hydrogen fluoride is present in the sample, wherein said silylated organic compound is:

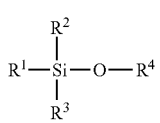

in which $R^1$, $R^2$ and $R^3$ are independently selected from $C_1$ to $C_6$ alkyls and $R^4$ is an organic compound.

2. The method as claimed in claim 1, in which $R^1$, $R^2$ and $R^3$ are independently selected from the group consisting of methyl, ethyl, propyl and butyl.

3. The method as claimed in claim 1, in which the organic compound is a hydroxylated compound having a molecular weight of from 250 to 200,000 g.mol$^{-1}$.

4. The method as claimed in claim 1, in which the organic compound is a hydroxylated compound selected from the group consisting of estradiol, peptides, homovanillic acid, amphotericin, steroids, cytokines, arachidonic acid and derivatives thereof.

5. The method as claimed in claim 1, in which the detection and/or measurement, in said measurement solution, of the appearance of the desilylated organic compound, or of the disappearance of the silylated organic compound, is carried out by means of gas chromatography.

6. The method as claimed in claim 1, in which the detection and/or the measurement, in said measurement solution, of the appearance of the desilylated organic compound, or of the disappearance of the silylated organic compound, is carried out by means of an immunological test using one or more antibodies which is/are directed either against the desilylated organic compound or the silylated organic compound.

7. The method as claimed in claim 6, in which the antibody(ies) is/are (a) monoclonal antibody(ies).

8. The method as claimed in claim 6, in which the immunological test is a competitive-type or non-competitive-type immunoassay.

9. The method as claimed in claim 1, in which the organic compound is estradiol or one of its derivatives.

10. The method as claimed in claim 1, in which the organic compound is selected from the group consisting of estra-1,3,5-triene-3,17 μ or 17 μ-diol, and their derivatives.

11. The method as claimed in claim 1, in which the silylated organic compound is used at a concentration of from 1 to 2000 ng/ml in the contacting step.

12. The method as claimed in claim 1, in which the aqueous solution is buffered to pH 4.5 to 5.5.

13. The method as claimed in claim 1, in which the contacting is effected at a temperature of from 54 to 64° C.

* * * * *